US010842806B2

(12) United States Patent
Vavvas et al.

(10) Patent No.: US 10,842,806 B2
(45) Date of Patent: Nov. 24, 2020

(54) METHODS FOR TREATING OCULAR INFLAMMATORY DISORDERS

(71) Applicant: Massachusetts Eye and Ear Infirmary, Boston, MA (US)

(72) Inventors: Demetrios G. Vavvas, Boston, MA (US); Joan W. Miller, Winchester, MA (US); Lucia Sobrin, Boston, MA (US); Jun Suzuki, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 190 days.

(21) Appl. No.: 15/624,172

(22) Filed: Jun. 15, 2017

(65) Prior Publication Data
US 2018/0036329 A1 Feb. 8, 2018

Related U.S. Application Data

(63) Continuation of application No. 14/129,708, filed as application No. PCT/US2012/044409 on Jun. 27, 2012, now abandoned.

(60) Provisional application No. 61/597,258, filed on Feb. 10, 2012, provisional application No. 61/501,586, filed on Jun. 27, 2011.

(51) Int. Cl.
*A61K 31/7056* (2006.01)

(52) U.S. Cl.
CPC ................................ *A61K 31/7056* (2013.01)

(58) Field of Classification Search
None
See application file for complete search history.

(56) References Cited

U.S. PATENT DOCUMENTS

| | | | |
|---|---|---|---|
| 4,575,498 | A | 3/1986 | Holmes et al. |
| 5,082,829 | A | 1/1992 | Gruber et al. |
| 5,443,505 | A | 8/1995 | Wong et al. |
| 5,766,242 | A | 6/1998 | Wong et al. |
| 5,777,100 | A | 7/1998 | Bullough et al. |
| 6,251,090 | B1 | 6/2001 | Avery et al. |
| 6,299,895 | B1 | 10/2001 | Hammang et al. |
| 6,375,972 | B1 | 4/2002 | Guo et al. |
| 6,413,540 | B1 | 7/2002 | Yaacobi |
| 6,416,777 | B1 | 7/2002 | Yaacobi |
| 2007/0270350 | A1 | 11/2007 | Singh |
| 2011/0112047 | A1 | 5/2011 | Evans et al. |
| 2015/0005254 | A1 | 1/2015 | Vavvas |

FOREIGN PATENT DOCUMENTS

| WO | WO-2000/040089 A1 | 7/2000 |
|---|---|---|
| WO | WO-2001/028474 A1 | 4/2001 |
| WO | WO-2001/093873 A1 | 12/2001 |
| WO | WO-2002/089767 A1 | 11/2002 |
| WO | WO-2007/014327 A2 | 2/2007 |
| WO | WO-2010/073011 A2 | 7/2010 |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596. (Year: 1996).*
Suzuki et al., Investigative Ophthalmology & Visual Science, Apr. 2011, vol. 52, pp. 2943 (Year: 2011).*
Amadi-Obi A et al., (2007) 'TH17 Cells Contribute to Uveitis and Scleritis and are Expanded by IL-2 and Inhibited by IL-27/STAT1,' Nat Med, 13(6):711-8.
Ambati J et al., (2000) 'Diffusion of High Molecular Weight Compounds Through Sclera,' Invest Ophthalmol Vis Sci, 41(5):1181-5.
Ambati J et al., (2000) 'Transscleral Delivery of Bioactive Protein to the Choroid and Retina,' Invest Ophthalmol Vis Sci, 41(5):1186-91.
ARVO/ISOCB 2011 Meeting Abstract, Suzuki J et al., (2011) 'Inhibitory Effect of Aicar on Endotoxin-Induced Uveitis in Rats,' Invest Ophthalmol Vis Sci, 52(14):2943.
Avunduk MC et al., (2004) 'Etanercept Treatment in the Endotoxin-induced Uveitis of Rats,' Exp Eye Res, 79(3):357-65.
Baeuerle Pa and Henkel T, (1994) 'Function and Activation of NF-κB in the Immune System,' Annu Rev Immunol, 12:141-79.
Bagenstose LM et al., (2005) 'Disruption of CD40/CD40-ligand Interactions in a Retinal Autoimmunity Model Results in Protection Without Tolerance,' J Immunol, 175(1):124-30.
Baldwin AS Jr, (1996) 'The NF-κβ and Ικβ Proteins: New Discoveries and Insights,' Annu Rev Immunol, 14:649-83.
Becker MD et al., (2001) 'Inhibition of Leukocyte Sticking and Infiltration, but not Rolling, by Antibodies to ICAM-1 and LFA-1 in Murine Endotoxin-induced Uveitis,' Invest Ophthalmol Vis Sci, 42(11):2563-6.
Campàs C et al., (2003) 'Acadesine Activates AMPK and Induces Apoptosis in B-Cell Chronic Lymphocytic Leukemia Cells but not in T Lymphocytes,' Blood, 101(9):3674-80.
Caspi RR, (2008) 'Autoimmunity in the Immune Privileged Eye: Pathogenic and Regulatory T Cells,' Immunol Res, 42(1-3):41-50.
Cell Signalling Technology, 'Product Pathways—Glucose Metabolism AICAR #9944,' Product Information Sheet, Cell Signaling Technology, Danvers, MA (Publ), retrieved from the internet at http://www.cellsignal.com/products/9944.html> 3 pages.
Chang JH et al., (2006) 'Toll-like Receptors in Ocular Immunity and the Immunopathogenesis of Inflammatory Eye Disease,' Br J Ophthalmol, 90(1):103-8.
Cuthbertson DJ et al., (2007) '5-Aminoimidazole-4-carboxamide 1-β-D-ribofuranoside Acutely Stimulates Skeletal Muscle 2-Deoxyglucose Uptake in Healthy Men,' Diabetes, 56(8):2078-84.
Durrani OM et al., (2004) 'Degree, Duration, and Causes of Visual Loss in Uveitis,' Br J Ophthalmol, 88(9):1159-62.
Durrani OM et al., (2004) 'Uveitis: A Potentially Blinding Disease,' Ophthalmologica, 218(4):223-36.

(Continued)

*Primary Examiner* — Traviss C McIntosh, III
(74) *Attorney, Agent, or Firm* — Goodwin Procter LLP

(57) ABSTRACT

Provided are methods for treating ocular inflammatory disorders, including macular edema, using an AMP kinase activator, e.g., 5-aminoimidazole-4-carboxamide-1-β-d-ribofuranoside (AICAR). The method reduces inflammation, thereby minimizing the loss of vision or visual function associated with these ocular disorders.

15 Claims, 15 Drawing Sheets

(56) References Cited

OTHER PUBLICATIONS

Fuentes ME et al., (1995) 'Controlled Recruitment of Monocytes and Macrophages to Specific Organs through Transgenic Expression of Monocyte Chemoattractant Protein-1,' J Immunol, 155(12):5769-76.

Fukai T et al., (1999) 'The Role of Costimulatory Molecules B7-1 and B7-2 in Mice with Experimental Autoimmune Uveoretinitis,' Graefes Arch Clin Exp Ophthalmol, 237(11):928-33.

Gaidhu MP et al., (2009) 'Prolonged Aicar-Induced AMP-Kinase Activation Promotes Energy Dissipation in White Adipocytes: Novel Mechanisms Integrating HSL and ATGL,' J Lipid Res, 50(4):704-15.

Galor A et al., (2008) 'Comparison of Antimetabolite Drugs as Corticosteroid-sparing Therapy for Noninfectious Ocular Inflammation,' Ophthalmology, 115(10):1826-32.

Giri S et al., (2004) '5-Aminoimidazole-4-carboxamide-1-?-4-ribofuranoside Inhibits Proinflammatory Response in Glial Cells: A Possible Role of AMP-Activated Protein Kinase,' J Neurosci, 24(2):479-87.

Hardie DG and Carling D, (1997) 'The AMP-Activated Protein Kinase—Fuel Gauge of the Mammalian Cell?,' Eur J Biochem, 246(2):259-73.

Hardie DG et al., (1998) 'The AMP-Activated/SNF-1 Protein Kinase Subfamily: Metabolic Sensors of the Eukaryotic Cell?,' Annu Rev Biochem, 67:821-55.

Hardie DG et al., (2003) 'Management of Cellular Energy by the AMP-activated Protein Kinase System,' FEBS Lett, 546(1):113-20.

Herbort CP et al., (1989) 'Immunopharmacological Analysis of Endotoxin-induced Uveitis in the Rat,' Exp Eye Res, 48(5):693-705.

Hoekzema R et al., (1991) 'Analysis of Interleukin-6 in Endotoxin-Induced Uveitis,' Invest Ophthalmol Vis Sci, 32(1):88-95.

Imrie FR and Dick AD, (2007) 'Biologics in the Treatment of Uveitis,' Curr Opin Ophthalmol, 18(6):481-6.

International Search Report for PCT/US2012/044409, dated Jan. 11, 2013 (6 pages).

Janeway CA Jr and Bottomly K, (1994) 'Signals and Signs for Lymphocyte Responses,' Cell, 76(2):275-85.

Jantzen and Robinson, 'B. Prodrugs,' *Modern Pharmaceutics*, (3rd Ed, 2002), GS Banker and CT Rhodes (Eds), Marcel Dekker, Inc., New York, NY (Pub), p. 596.

Jenkins MK, (1994) 'The Ups and Downs of T Cell Costimulation,' Immunity, 1(6):443-6.

Jhun BS et al., (2004) '5-Aminoimidazole-4-carboxamide Riboside Suppresses Lipopolysaccharide-Induced TNF-? Production through Inhibition of Phosphatidylositol 3-Kinase/Akt Activation in RAW 264.7 Murine Macrophages,' Biochem Biophys Res Commun, 318(2):372-80.

Jørgensen SB et al., (2004) 'Knockout of the $\alpha_2$ but not $\alpha_1$ 5'AMP-activated Protein Kinase Isoform Abolishes 5-aminoimidazole-4-carboxamide-1-6-4-ribofuranoside, but not Contraction-induced Glucose Uptake in Skeletal Muscle,' J Biol Chem, 279(2):1070-9.

Katerelos M et al., (2010) '5-Aminoimidazole-4-carboxamide Ribonucleoside and AMP-Activated Protein Kinase Inhibit Signalling through NF-??,' Immunol Cell Biol, 88(7):754-60.

Keino H et al., (2007) 'Supplementation of CD4+CD25+ Regulatory T Cells Suppresses Experimental Autoimmune Uveoretinitis,' Br J Ophthalmol, 91(1):105-10.

Koizumi K et al., (2003) 'Contribution of TN-α to Leukocyte Adhesion, Vascular Leakage, and Apoptotic Cell Death in Endotoxin-induced Uveitis in vivo,' Invest Ophthalmol Vis Sci, 44(5):2184-91.

Krawczyk CM et al., (2010) 'Toll-like Receptor-induced Changes in Glycolytic Metabolism Regulate Dendritic Cell Activation,' Blood, 115(23):4742-9.

Kuo CL et al., (2008) 'Inhibition of Lipopolysaccharide-Induced Inducible Nitric Oxide Synthetase and Cyclooxygenase-2 Gene Expression by 5-Aminoimidazole-4-carboxamide Riboside is Independent of AMP-Activated Protein Kinase,' J Cell Biochem, 103(3):931-40.

Labuzek K et al., (2010) 'AICAR (5-aminoimidazole-4-carboxamide-1-β-4-ribofuranoside) Increases the Production of Toxic Molecules and Affects the Profile of Cytokines Release in LPS-Stimulated Rat Primary Microglial Cultures,' Neurotoxicology, 31(1):134-46.

Landmann R et al., (1996), 'Human Monocyte CD14 is Upregulated by Lipopolysaccharide,' Infect Immun, 64(5):1762-9.

Lardenoye CW et al., (2006) 'Impact of Macular Edema on Visual Acuity in Uveitis,' Ophthalmology, 113(8):1446-9.

Longnus SL et al., (2003) '5-Aminoimidazole-4-carboxamide 1-?-D-ribofuranoside (AICAR) Stimulates Myocardial Glycogenolysis by Allosteric Mechanisms,' Am J Physiol Regul Integr Comp Physiol, 284(4):R936-44.

Luger D and Caspi RR, (2008) 'New Perspective on Effector Mechanisms in Uveitis,' Semin Immunopathol, 30(2):135-43.

Mangano DT et al., (2006) 'Post-Reperfusion Myocardial Infarction: Long-Term Survival Improvement Using Adenosine Regulation with Acadesine,' J Am Coll Cardiol, 48(1):206-14.

Manola A et al., (2010) 'AICAR (5-Aminoimidazole-4-Carboxamide-1-Beta-D-Ribofuranoside) Ameliorates Inflammation in the Endotoxin Induced Uveitis Model,' ARVO 2010 Annual Meeting Abstract, Invest Ophthalmol Vis Sci. 51:5235 (2 pages).

Namba K et al., (2000) 'Amelioration of Experimental Autoimmune Uveoretinitis by Pretreatment with a Pathogenic Peptide in Liposome and Anti-CD40 Ligand Monoclonal Antibody,' J Immunol, 165(6):2962-9.

Narkar VA et al., (2008) 'AMPK and PPARδ Agonists are Exercise Mimetics,' Cell, 134(3):405-15.

Nath N et al., (2005) '5-aminoimidazole-4-carboxamide Ribonucleoside: A Novel Immunomodulator with Therapeutic Efficacy in Experimental Autoimmune Encephalomyelitis,' J Immunol, 175(1):566-74.

Pot C et al., (2011) 'Type 1 Regulatory T Cells (Tr1) in Autoimmunity,' Semin Immunol, 23(3):202-8. NIH Public Access Author Manuscript.

Poulaki V et al., (2007) 'Inhibition of Hsp90 Attenuates Inflammation in Endotoxin-induced Uveitis,' FASEB J, 21(9):2113-23.

Pouvreau I et al., (1998) 'Effect of Macrophage Depletion by Liposomes Containing Dichloromethylene-diphosphonate on Endotoxin-induced Uveitis,' J Neuroimmunol, 86(2):171-81.

Prasad R et al., (2006) '5-Aminoimidazole-4-carboxamide-1-beta-4-ribofuranoside Attenuates Experimental Autoimmune Encephalomyelitis via Modulation of Endothelial-Monocyte Interaction,' J Neurosci Res, 84(3):614-25.

Qin S et al., (2008) 'Implication of S-Adenosylhomocysteine Hydrolase in Inhibition of TNF-α and IL-1β-Induced Expression of Inflammatory Mediators by AICAR in RPE Cells,' Invest Ophthalmol Vis Sci, 49(3):1274-81.

Rizzo LV et al., (1996), 'Establishment and Characterization of a Murine CD4+ T Cell Line and Clone that Induces Experimental Autoimmune Uveoretinitis in B10.A Mice,' J Immunol 156(4):1654-60.

Rosenbaum JT et al., (1980) 'Endotoxin-Induced Uveitis in Rats as a Model for Human Disease,' Nature, 286(5773):611-3.

Sag D et al., (2008) 'Adenosine 5'-Monophosphate-activated Protein Kinase Promotes Macrophage Polarization to an Anti-inflammatory Functional Phenotype,' J Immunol, 181(12):8633-41.

Sanui H et al., (1989) 'Identification of an Immunodominant and Highly Immunopathogenic Determinant in the Retinal Interphotoreceptor Retinoid-binding Protein (IRBP),' J Exp Med, 169(6):1947-60.

Sintzel MB et al., (1996) 'Biomaterials in Ophthalmic Drug Delivery,' Eur J Pharm Biopharm, 42(6):358-74.

Sun M et al., (2010) 'Contribution of CD4+CD25+ T Cells to the Regression Phase of Experimental Autoimmune Uveoretinitis,' Invest Ophthalmol Vis Sci, 51(1):383-9.

Suzuki J et al., (2011) 'Inhibitory Effect of Aminoimidazole Carboxamide Ribonucleotide (AICAR) on Endoctoxin-induced Uveitis in Rats,' Invest Ophtahlmol Vis Sci, 52(9):6565-71.

Suzuki J et al., (2012) 'Aminoimidazole Carboxamide Ribonucleotide Ameliorates Experimental Autoimmune Uveitis,' Invest Ophthalmol Vis Sci, 53(7):4158-69.

(56) References Cited

OTHER PUBLICATIONS

Sánchez-Lemus E et al., (2009) 'Angiotensin II AT1 Blockage Reduces the Lipopolysaccharide-induced Innate Immune Response in Rat Spleen,' Am J Physiol Regul Integr Comp Physiol, 296(5):R1376-84.

Takeda K et al., (2003) 'Toll-like Receptors,' Annu Rev Immunol, 21:335-76.

Takeuchi M et al., (2001) 'Differentiation of Thi and Th2 Cells in Lymph Nodes and Spleens of Mice During Experimental Autoimmune Uveoretinitis,' Jpn J Ophthalmol, 45(5):463-9.

Theodoropoulou S et al., (2010) 'Retinoblastoma Cells are Inhibited by Aminoimidazole Carboxamide Ribonucleotide (AICAR) Partially through Activation of AMP-Dependent Kinase,' FASEB J, 24(8):2620-30.

Tuaillon N et al., (2002) 'MCP-1 Expression in Endotoxin-Induced Uveitis,' Invest Ophthalmol Vis Sci, 43(5):1493-8.

Wakefield D et al., (2010) 'The Role of PAMPs and DAMPs in the Pathogenesis of Acute and Recurrent Anterior Uveitis,' Br J Ophthalmol, 94(3)271-4.

Winder WW and Hardie DG, (1999) 'AMP-Activated Protein Kinase, a Metabolic Master Switch: Possible Roles in Type-2 Diabetes,' Am J Physiol, 277(1 Pt 1):E1-10.

Written Opinion of the International Searching Authority for PCT/US2012/044409, dated Jan. 11, 2013 (12 pages).

Yang L et al., (2005) 'ICAM-1 Regulates Neutrophil Adhesion and Transcellular Migration of the TNF-α-Activated Vascular Endothelium Under Flow,' Blood, 106(2):584-92.

Yoshimura T et al., (2008) 'Differential Roles for INF-γ and IL-17 in Experimental Autoimmune Uveoretinitis,' Int Immunol, 20(2):209-14.

Zhao X et al., (2008) 'Activation of AMPK Attenuates Neutrophil Proinflammatory Activity and Decreases the Severity of Acute Lung Injury,' Am J Physiol Lung Cell Mol Physiol, 295(3):L497-504.

Zhu G et al., (2000) 'Stabilization of Proteins Encapsulated in Injectable Poly(lactide-co-glycolide),' Nat Biotechnol, 18(1):52-7.

ME Wolff, Chapter 9: Some Considerations for Prodrug Design, *Burger's Medical Chemistry and Druci Discovery, vol. I: Principles and Practice*, (5th Ed, 1995), ME Wolf (Ed), John Wiley & Sons, Inc., New York, NY (Publ), pp. 975-977.

\* cited by examiner

METHODS FOR TREATING OCULAR INFLAMMATORY DISORDERS

CROSS REFERENCE TO RELATED APPLICATIONS

This application is a continuation of U.S. patent application Ser. No. 14/129,708, filed Aug. 12, 2014, which is the national stage of International (PCT) Patent Application No. PCT/US2012/044409, filed Jun. 27, 2012, which claims the benefit of and priority to U.S. Provisional Patent Application No. 61/501,586, filed Jun. 27, 2011, and U.S. Provisional Patent Application No. 61/597,258, filed Feb. 10, 2012, the contents of each of which are hereby incorporated by reference in their entirety, for all purposes.

FIELD OF THE INVENTION

The present invention relates generally to the field of ocular inflammatory disorders. More particularly, the invention relates to methods for treating such disorders using an AMP kinase activator, e.g., 5-aminoimidazole-4-carboxamide-1-β-d-ribofuranoside (AICAR).

BACKGROUND OF THE INVENTION

There are a variety of ocular inflammatory disorders, which, if untreated, may lead to partial or even complete vision loss. One prominent ocular inflammatory disorder is uveitis, which is estimated to be responsible for approximately 10% of the blindness in the United States. Uveitis is an inflammatory eye disorder of the uveal tract and contiguous structures including the vascular coat of the eye composed of the iris, ciliary body and choroid (Durrani et al. (2004) BR. J OPHTHALMOL. 88:1159-1162; Durrani et al. (2004) OPHTHALMOLOGICA 218:223-236). Other examples of ocular inflammatory disorders include endophthalmitis (e.g., the endogenous form and the exogenous form), macular edema (e.g., macular edema that occurs as a result of age-related macular degeneration, cataract surgery, diabetes, drug toxicity, eye injury, or retinal vein occlusion), conjunctivitis, episcleritis, keratitis, optic neuritis, orbital pseudotumor, retinal vasculitis, and scleritis. Each of these disorders, if left untreated, can cause permanent vision loss.

Available treatments for uveitis and other ocular inflammatory disorders are limited. Corticosteroids are the main drugs used for its treatment but they have numerous ocular (cataract and secondary glaucoma) and non-ocular adverse effects. Prolonged systemic steroid use can also suppress musculoskeletal growth, cause impaired wound healing, and result in increased susceptibility to infections. In addition to corticosteroids, antimetabolites, cycloplegics, and biologics are also often used to control the inflammatory process. However, there are patients who do not respond or cannot tolerate these agents (Galor et al. (2008) OPHTHALMOLOGY 115:1826-1832; Imrie et al. (2007) CURR. OPIN. OPHTHALMOL. 18:481-486).

Thus, there is still an ongoing need for methods of preventing the onset of ocular inflammatory disorders, and once established, the treatment of such disorders.

SUMMARY OF THE INVENTION

The invention is based, in part, on the discovery that an AMP kinase activator, e.g., 5-aminoimidazole-4-carboxamide-1-β-d-ribofuranoside (AICAR) can be used to prevent and/or treat ocular inflammatory disorders, such as macular edema, uveitis (e.g., autoimmune uveitis and uveitis associated with type II, type III, type IV, or type V hypersensitivity reactions), and endophthalmitis. The disclosed methods comprise administering AICAR or a pharmaceutically acceptable salt, ester, prodrug, or polymorph thereof to a subject in need thereof in an amount sufficient to ameliorate a symptom of the disorder, e.g., to reduce ocular inflammation in the affected eye or part of the eye. In exemplary embodiments, the AICAR is administered to the eye, e.g., by intraocular injection or by topical administration to the eye.

The foregoing aspects and embodiments of the invention may be more fully understood by reference to the following figures, detailed description and claims.

BRIEF DESCRIPTION OF THE DRAWINGS

The objects and features of the invention may be more fully understood by reference to the drawings described herein.

FIG. 1A is a graph showing the clinical inflammation scores of EIU in Lewis rats in the absence and presence of AICAR determined at 24 hours after lipopolysaccharide (LPS) injection. (Normal: n=6, EIU: n=15, LPS+AICAR 50 mg/kg: n=15, LPS+AICAR 100 mg/kg: n=12). Data are shown as mean±SD; *$p<0.05$ and ***$p<0.001$. FIG. 1B provides photographs indicating that fibrin formation and posterior synechiae were seen less in AICAR-pretreated EIU rats. FIG. 1C provides histopathologic findings of EIU rat's eyes which received LPS with and without 50 mg/kg of AICAR pretreatment. The number of leukocytes infiltrated around the iris-ciliary body was suppressed in AICAR pretreated rats. Sections were visualized at 200×.

FIG. 2A is a graph depicting the number of infiltrated cells as determined by trypan blue exclusion cell counting. FIG. 2B is a graph depicting the total protein concentration in the aqueous humor (Normal: n=7, AICAR: n=6, LPS: n=1, LPS with AICAR: n=11). LPS induced cellular infiltration and protein leakage in the aqueous humor were significantly suppressed by AICAR pretreatment. Data are shown as mean±SD; **$p<0.01$.

FIG. 3A is a graph showing the number of retinal adherent leukocytes (Normal: n=5, AICAR: n=6, LPS: n=8, LPS with AICAR: n=11). AICAR-pretreated EIU rats showed significantly fewer adherent leukocytes than PBS-treated rats. FIG. 3B provides photographs of flatmounted retinas from normal control rats treated with AICAR, LPS only and LPS with AICAR pretreatment. EIU rats revealed a significant number of leukocyte adhesion (arrows) compared to AICAR pretreated rats. Data are shown as mean±SD; **$p<0.01$.

FIG. 5A is a graph showing CD14 mRNA expression as measured by ELISA (Normal: n=6, AICAR: n=6, LPS: n=9, LPS with AICAR: n=9). Data are shown as mean±SD; *$p<0.05$ and **$p<0.01$. FIG. 5B depicts photographs showing protein levels of CD14 as determined by Western blot analysis. Data are representative of three independent experiments with similar results.

FIG. 6A is a graph showing EAU clinical score as assessed by funduscopic examination at 21 days after immunization. (Controls: open circles, n=17; AICAR 100 mg/kg: closed circles, n=10; AICAR 200 mg/kg: closed triangles, n=15). FIG. 6B is a graph showing histopathologic score as assessed with hematoxylin and eosin (H&E) sections. Mean scores are indicated by horizontal bars. FIGS. 6C-6F show representative fundus photographs and histopathological findings of vehicle-treated EAU mice (FIGS. 6C and 6E) and AICAR-treated (200 mg/kg) mice (FIGS. 6D and 6F). Clinical papilledema and vasculitis (FIG. 6C) as well as histopathological cellular infiltration, papilledema and retinal folds (FIG. 6E) were seen in vehicle-treated EAU mice. Data are shown as mean±SD; *** $p<0.001$. Results were combined from three separate experiments.

FIG. 7A provides graphs showing TNF-α, IL-6 and IFN-γ gene expression in the retina as measured by real-time PCR. Relative expression was normalized to beta-actin (naïve wildtype mice: n=3, control untreated EAU mice: n=5, AICAR treated EAU mice: n=5). FIG. 7B provides graphs showing TNF-α, IL-6 and IFN-γ protein levels in the retina as assessed by ELISA (control: n=10, AICAR: n=10). Data are shown as mean±SD and is representative of two to three independent experiments. *$p<0.05$, **$p<0.01$. N.D.=not detectable.

FIGS. 8C, 8D, 8E, and 8F depict graphs showing production of IFN-γ, IL-17, IL-4, and IL-10, respectively, as measured by ELISA. FIGS. 8G and 8H depict graphs showing T-bet and RORγt mRNA expression, respectively, in CD4 T cells, as measured by real-time PCR. Relative expression was normalized to beta-actin (n=6 to 8). Data are expressed as mean±SD and representative of two to three independent experiments. *$p<0.05$, **$p<0.01$.

FIG. 12A provides graphs showing the number of CD11c-gated CD40, CD80, CD86 and I-A$^b$ positive cells as measured by FACS. Bars represent mean±SD from three independent experiments. FIG. 12B provides graphs showing IL-6, IL-12/23 p40 and TNF-α production as measured by ELISA. Data are expressed as mean±SD and representative of two independent experiments. *$p<0.05$, **$p<0.01$.

FIG. 14A provides graphs showing the number of CD11c-gated CD40, CD80, CD86 and I-A$^b$ positive cells as measured by FACS. Bars represent mean±SD from 3 independent experiments. FIG. 14B depicts graphs showing IL-6, IL-12/23 p$^{40}$ and TNF-α production as measured by ELISA. Data are expressed as mean±SD and representative of two independent experiments. *$p<0.05$, **$p<0.01$.

DETAILED DESCRIPTION

Figure 1A:
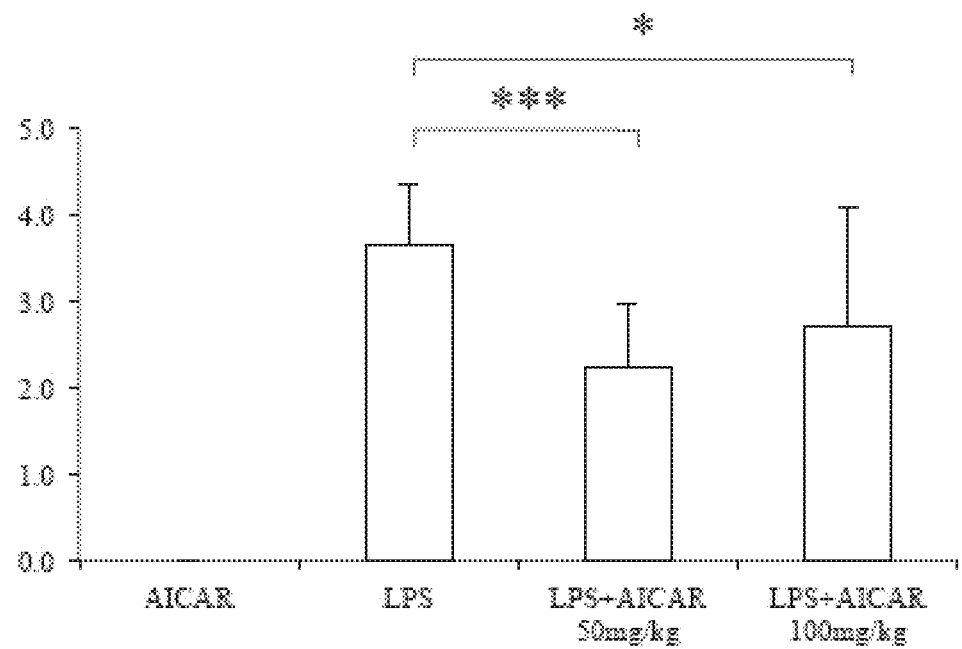
FIGS. 1A-1C depict the effect of AICAR on clinical endotoxin-induced uveitis (EIU).

The invention relates to methods for treating and/or preventing ocular inflammatory disorders using AMP kinase (AMPK) activators, e.g., 5-aminoimidazole-4-carboxamide-1-β-d-ribofuranoside (AICAR). The invention is based, at least in part, on the discovery that AMP kinase activators, e.g., AICAR, suppress ocular inflammation, e.g., uveitis-related ocular inflammation.

For convenience, certain terms in the specification, examples, and appended claims are collected in this section.

As used herein, "AMP kinase activator" or "adenosine monophosphate (AMP) kinase activator" refers to compounds that activate, increase, or stimulate AMP kinase activity. AMP kinase activators include 5-aminoimidazole-4-carboxamide-1-β-d-ribofuranoside (AICAR) or pharmaceutically acceptable salts, esters, or polymorphs thereof, AICAR analogs and/or AICAR prodrugs. For example, AICAR is an analog of AMP.

One exemplary AMP kinase activator is AICAR or a pharmaceutically acceptable salt thereof. As used herein, "AICAR" means 5-aminoimidazole-4-carboxamide-1-β-d-ribofuranoside and having the following chemical structure (I):

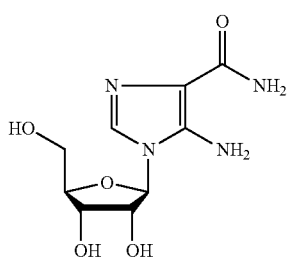

including pharmaceutically acceptable salts, solvates, solvates of a pharmaceutically acceptable salt, esters, or polymorphs thereof. See, for example, U.S. Pat. No. 4,575,498.

In another embodiment, the AMP kinase activator is an AICAR prodrug. A "prodrug" includes compounds that are transformed in vivo to yield a compound of Formula (I) or a pharmaceutically acceptable salt, ester, or polymorph of the compound. The transformation may occur by various mechanisms, such as through hydrolysis in blood. For example, where the compound of Formula (I) contains an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate). Further, for example, where the compound of Formula (I) incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$ alkyl, carboxy$(C_1-C_6)$alkyl, amino$(C_1-C_4)$alkyl or mono-N- or di-N,N—$(C_1-C_6)$alkylaminoalkyl, —$C(Y^4)Y^5$ wherein $Y^4$ is H or methyl and $Y^5$ is mono-N- or di-N,N—$(C_1-C_6)$ alkylamino, morpholino, piperidin-1-yl or pyrrolidin-1-yl. Exemplary AICAR prodrugs include the generic and/or specific compounds listed in U.S. Pat. No. 5,082,829, which is incorporated herein by reference in its entirety.

It is also contemplated herein that generic and/or specific compounds listed in U.S. Pat. No. 5,777,100 and PCT Publication No. WO01/93873, which are incorporated herein by reference in their entirety, may be used in the methods described herein.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts or esters.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "therapeutically effective amount" is understood to mean the amount of an active ingredient, for example, AICAR, that is sufficient to reduce, ameliorate, or treat a symptom associated with certain ocular inflammatory disorders described herein, e.g., a symptom of the condition affecting any part of the eye or surrounding tissue. The compounds of the invention are administered in amounts effective at, e.g., reducing or preventing inflammation in at least part of an affect eye or the surrounding tissues, preserving vision, improving vision, and/or preventing vision loss.

Disclosed herein is a method of treating ocular inflammatory disorders using AMP kinase activators, e.g., 5-aminoimidazole-4-carboxamide-1-β-d-ribofuranoside (AICAR) or a pharmaceutically acceptable salt thereof, an AICAR analog, and/or an AICAR prodrug. Ocular inflammatory conditions that may be treated with AICAR include, but are not limited to endophthalmitis (e.g., the endogenous form and the exogenous form), macular edema (e.g., macular edema that occurs as a result of age-related macular degeneration, cataract surgery, diabetes, drug toxicity, eye injury, retinal vein occlusion, or other inflammatory eye diseases), conjunctivitis, episcleritis, keratitis, optic neuritis, orbital pseudotumor, retinal vasculitis, scleritis, and uveitis (e.g., (i) uveitis associated with sepsis (e.g., LPS-induced uveitis); (ii) autoimmune uveitis (e.g., uveitis associated with lupus);

or (iii) uveitis associated with type II, type III, type IV, or type V hypersensitivity reactions).

It is contemplated herein that the AICAR may be administered after diagnosis of certain ocular inflammatory conditions described herein, at the time of diagnosing certain ocular inflammatory conditions described herein or, if the subject is determined to be a risk of developing certain ocular inflammatory conditions as described herein, the AICAR may be administered prior to diagnosis of the condition.

In certain embodiments, the method comprises administering AICAR to the eye of a subject in which a region of eye has been affected by inflammation. The AICAR may be administered in an amount sufficient to give a final concentration of AICAR in the eye in the range from about 1 µM to about 2500 µM, from about 1 µM to about 2000 µM, from about 1 µM to about 1500 µM, from about 1 µM to about 1000 µM, from about 10 µM to about 900 µM, from about 100 µM to about 900 µM, from about 200 µM to about 800 µM, or from about 300 µM to about 500 µM.

In view of the fact that the volume of the eye in a given subject is known (for example, typical human eye contains 4 to 6 mL of fluid (humor)) it is within the skill in the art to calculate the dosage of the AICAR to be administered to give the therapeutically effective concentrations noted above. In other embodiments, an effective amount of AICAR may be in the range of from about 0.01 mg/kg to about 500 mg/kg, optionally from about 0.01 mg/kg to about 250 mg/kg, optionally from about 0.01 mg/kg to about 200 mg/kg, optionally from about 1.0 mg/kg to about 100 mg/kg, optionally from about 1 mg/kg to about 10 mg/kg, of body weight.

In therapeutic uses for treating ocular disorders, the active ingredients typically are administered orally, parenterally and/or topically at a dosage to obtain and maintain a concentration that is therapeutically effective in the eye. In certain circumstances, a therapeutically effective dose of AICAR prevents or reduces inflammation in at least part of an affected eye. The amount administered likely will depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue level, or the initial dosage may be smaller than the optimum and the daily dosage may be progressively increased during the course of treatment depending on the particular situation. If desired, the daily dose may also be divided into multiple doses for administration, for example, two to four times per day. For example, AICAR may be administered once a day, twice a day or more frequently. In other embodiments, AICAR may be administered every other day, three times a week, twice a week, or once a week.

In an exemplary embodiment, the AICAR may be administered locally to the eye, for example, by intravitreal, intraocular, intraorbital, periorbital, subconjuctival, subretinal, subtenons or transscleral routes. In an exemplary embodiment, the AICAR may be administered locally to the eye by intravitreal injection. Without wishing to be bound by theory, local modes of administration can reduce or eliminate the incidence of potential toxic side effects that may occur. In another embodiment, local administration to the eye is by topical administration.

Alternatively, the AICAR may be administered systemically, e.g., by oral or parenteral routes. Parenteral routes include, for example, intravenous, intrarterial, intramuscular, intradermal, subcutaneous, intranasal, intraperitoneal and transdermal routes.

Administration may be provided as a periodic bolus (for example, intravitreally or intravenously) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag, or a contact lens slow release formulation system). The AICAR may be administered locally, for example, by continuous release from a sustained release drug delivery device immobilized to an inner wall of the eye or via targeted transscleral controlled release into the choroid (see, for example, PCT/US00/00207, PCT/US02/14279, Ambati et al. (2000) INVEST. OPHTHALMOL. VIS. SCI. 41:1181-1185, and Ambati et al. (2000) INVEST. OPHTHALMOL. VIS. SCI. 41:1186-1191). A variety of devices suitable for administering agents locally to the inside of the eye are known in the art. See, for example, U.S. Pat. Nos. 6,251,090, 6,299,895, 6,416,777, 6,413,540, and 6,375,972, and PCT/US00/28187.

The formulations, both for human and for veterinary medical use, typically include AICAR in association with a pharmaceutically acceptable carrier or excipient.

The AICAR may be solubilized in a carrier, for example, a viscoelastic carrier, that is introduced locally into the eye. The AICAR also may be administered in a pharmaceutically acceptable carrier or vehicle so that administration does not otherwise adversely affect the recipient's electrolyte and/or volume balance. The carrier may comprise, for example, physiologic saline or other buffer system. In exemplary embodiments, the AICAR may be solubilized in PBS or another aqueous buffer by sonication. Alternatively, the AICAR may be solubilized using conventional solvent or solubilization systems, for example, dimethyl sulfoxide (DMSO), dimethoxyethane (DME), dimethylformamide (DMF), cyclodextran, micelles, liposomes, liposomal agents, and other solvents known in the art to aid in the solubilization and administration of hydrophobic agents.

In other embodiments, the AICAR may be solubilized in a liposome or microsphere. Methods for delivery of a drug or combination of drugs in liposomes and/or microspheres are well-known in the art.

In addition, it is contemplated that the AICAR may be formulated so as to permit release of the agent over a prolonged period of time. A release system can include a matrix of a biodegradable material or a material, which releases the incorporated agent by diffusion. The AICAR can be homogeneously or heterogeneously distributed within a release system. A variety of release systems may be useful in the practice of the invention, however, the choice of the appropriate system will depend upon the rate of release required by a particular drug regime. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, under certain circumstances, synthetic release systems are preferred because generally they are more reliable, more reproducible and produce more defined release profiles. The release system material can be selected so that inhibitors having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

One of the primary vehicles currently being developed for the delivery of ocular pharmacological agents is the poly (lactide-co-glycolide) microsphere for intraocular injection. The microspheres are composed of a polymer of lactic acid and glycolic acid, which are structured to form hollow spheres. These spheres can be approximately 15-30 µm in diameter and can be loaded with a variety of compounds varying in size from simple molecules to high molecular weight proteins such as antibodies. The biocompatibility of these microspheres is well established (see, Sintzel et al. (1996) EUR. J. PHARM. BIOPHARM. 42:358-372), and microspheres have been used to deliver a wide variety of pharmacological agents in numerous biological systems. After injection, poly(lactide-co-glycolide) microspheres are hydrolyzed by the surrounding tissues, which cause the release of the contents of the microspheres (Zhu et al. (2000) NAT. BIOTECH. 18:52-57). As will be appreciated, the in vivo half-life of a microsphere can be adjusted depending on the specific needs of the system.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

Formulations suitable for oral or parenteral administration may be in the form of discrete units such as capsules, gelatin capsules, sachets, tablets, troches, or lozenges, each containing a predetermined amount of the active agent; a powder or granular composition; a solution or a suspension in an aqueous liquid or non-aqueous liquid; or an oil-in-water emulsion or a water-in-oil emulsion. Formulations suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). Sterile injectable solutions can be prepared by incorporating the active compound in the required amount in an appropriate solvent with one or a combination of ingredients enumerated above, as required, followed by filter sterilization. Formulations suitable for intraarticular administration may be in the form of a sterile aqueous preparation of the drug which may be in microcrystalline form, for example, in the form of an aqueous microcrystalline suspension. Liposomal formulations or biodegradable polymer systems may also be used to present the drug for intraarticular administration. Formulations for topical administration to the skin surface can be prepared by dispersing the drug with a dermatologically acceptable carrier such as a lotion, cream, ointment or soap. For intranasal or inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations.

EXAMPLES

The invention is further illustrated by the following examples, which are provided for illustrative purposes only, and should not be construed as limiting the scope or content of the invention in any way.

In the examples described herein, all animal experiments adhered to the Association for Research in Vision and Ophthalmology Statement for the Use of Animals in Ophthalmic and Vision Research, and protocols were approved by the Animal Care Committee of the Massachusetts Eye and Ear Infirmary.

All results were expressed as mean±SD. EIU and EAU scores were compared by the Mann-Whitney test. Continuous variables from the other experiment were analyzed with the unpaired student's t test. Differences were considered significant at $P<0.05$.

Example 1: AICAR Treatment Suppresses Ocular Inflammation in a Rat EIU Model

Endotoxin-induced uveitis (EIU) is a rodent model of human uveitis, induced by a single systemic injection of endotoxin or lipopolysaccharide (LPS) (Rosenbaum et al., (1980) NATURE 286:611-613). Injected animals develop acute bilateral anterior inflammation, characterized by a breakdown of the blood-ocular barrier and accumulation of inflammatory cells. EIU has been used to investigate the pathogenesis of uveitis and to evaluate the therapeutic effect of several drugs (Herbort et al. (1989) EXP. EYE RES. 48:693-705; Avunduk et al. (2004) EXP. EYE RES. 79:357-365; Chang et al. (2006) BR. J. OPHTHALMOL. 90:103-108; Wakefield et al. (2010) BR. J. OPHTHALMOL. 94:271-274). The effect of AICAR on ocular inflammation associated with uveitis was assessed using the EIU rat model.

Male Lewis rats ranging from 6-8 weeks old (Charles River, Wilmington, Mass.) were used for these studies. To study the effects of AICAR pretreatment, AICAR and PBS (for placebo treatment) were delivered via intraperitoneal injection of AICAR (50 mg/kg or 100 mg/kg body weight; Sigma) diluted in 150 µl PBS or equal volume of PBS at 6 hours before and at the same time as LPS injection. Four experimental groups of rats were compared: (1) Normal: no treatment (2) AICAR: normal rats treated with AICAR 6 hours before examination; (3) LPS: EIU rats treated with PBS; (4) LPS+AICAR: EIU rats treated with AICAR. Two additional groups of rats were used to study the effects of AICAR (50 mg/kg) given either at the same time as LPS injection or at 6 hours after LPS injection.

Clinical scoring of EIU was performed as previously described (Pouvreau et al. (1998) J. NEUROIMMUNOL. 86:171-181). Slit lamp examination was conducted 24 hours after LPS injection in a masked fashion. The severity of EIU was graded from 0 to 4 by a masked investigator, using the following scale: 0=no inflammatory reaction; 1=discrete inflammation of the iris and conjunctival vessels; 2=dilation of the iris and conjunctival vessels with moderate flare in the anterior chamber; 3=hyperemia in iris associated with Tyndall effect in the anterior chamber; and 4=same clinical signs as 3 plus the presence of fibrin or synechiae.

For histopathologic evaluations, EIU rats were euthanized 24 hours after LPS injection. The eyes were enucleated immediately and stored in 10% formalin solution. The eyes were then embedded in paraffin, and 10 μm sagittal sections were cut and stained with hematoxylin and eosin. For histopathologic evaluation, the anterior chamber and posterior chamber around the iris-ciliary body complex were examined with light microscopy.

Figure 1B:
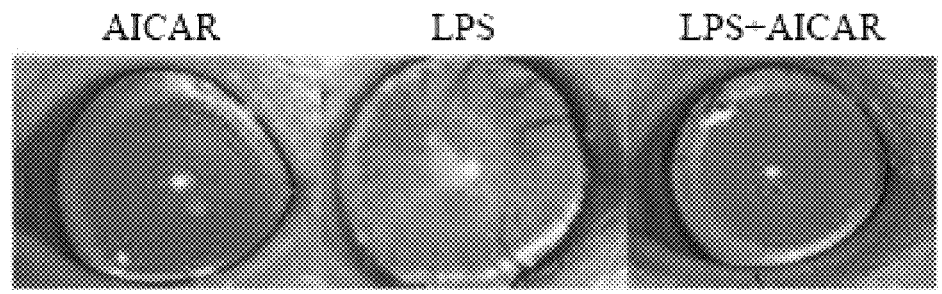
Figure 1C:
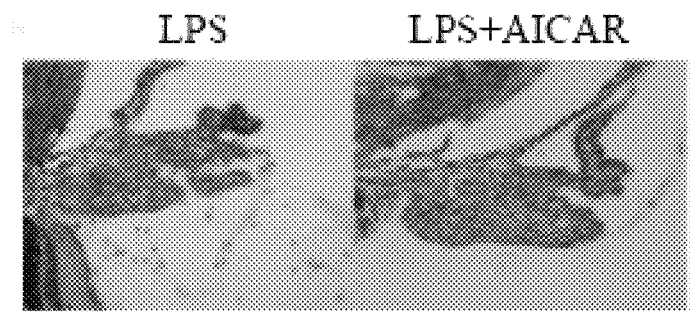

As depicted in FIG. 1A, clinical inflammation scores were significantly reduced in EIU rats pretreated with AICAR at either the 50 mg/kg dosage (2.2±0.75, n=15) or at the 100 mg/kg dosage (2.7±1.4, n=12) when compared with PBS-treated EIU rats (3.6±0.7, n=15) ($p=0.00008$ and 0.045, respectively). No inflammation was detected in age-matched normal rats that received AICAR alone (n=6). Further, fibrin formation and posterior synechiae were rarely seen in AICAR-pretreated EIU animals when compared to PBS-treated EIU rats or normal rats that received AICAR alone (FIG. 1B). Histopathological findings also revealed severe leukocyte infiltration in EIU rats compared to rats pretreated with AICAR (FIG. 1C).

The effects of a single dose of AICAR administered at the time of LPS injection or at 6 hours after LPS injection were also studied. With these alternative timing regimens, there was no suppression of inflammation compared with controls. EIU clinical scores were 3.7±0.5 (n=6) and 3.9±0.2 (n=6), respectively. Since pretreatment with AICAR at the 100 mg/kg dosage was not more effective in reducing inflammation than the 50 mg/kg dosage (no statistically significant difference, $p=0.347$), the remainder of the experiments were conducted with the 50 mg/kg dose.

Together, these data indicate that AICAR administration suppresses ocular inflammation in the rat EIU model as measured by slit lamp assessment and histopathology.

Example 2: AICAR Treatment Reduces Cell Infiltration into the Aqueous Humor

Aqueous humor was collected by anterior chamber puncture with a 30-gauge needle 24 hours after LPS injection. For cell counting, 1 μl of aqueous humor was diluted with an equal amount of Trypan-blue solution, and the cells were counted with a hematocytometer under a light microscope. A separate sample of aqueous humor was centrifuged at 2500 rpm for 5 minutes at 4° C. and the total protein concentration was measured by Lowry methods using a Bio-Rad protein assay kit (Hercules, Calif.). Aqueous samples were stored on ice until used; cell counts and total protein concentrations were measured on the day of sample collection.

Figure 2A:
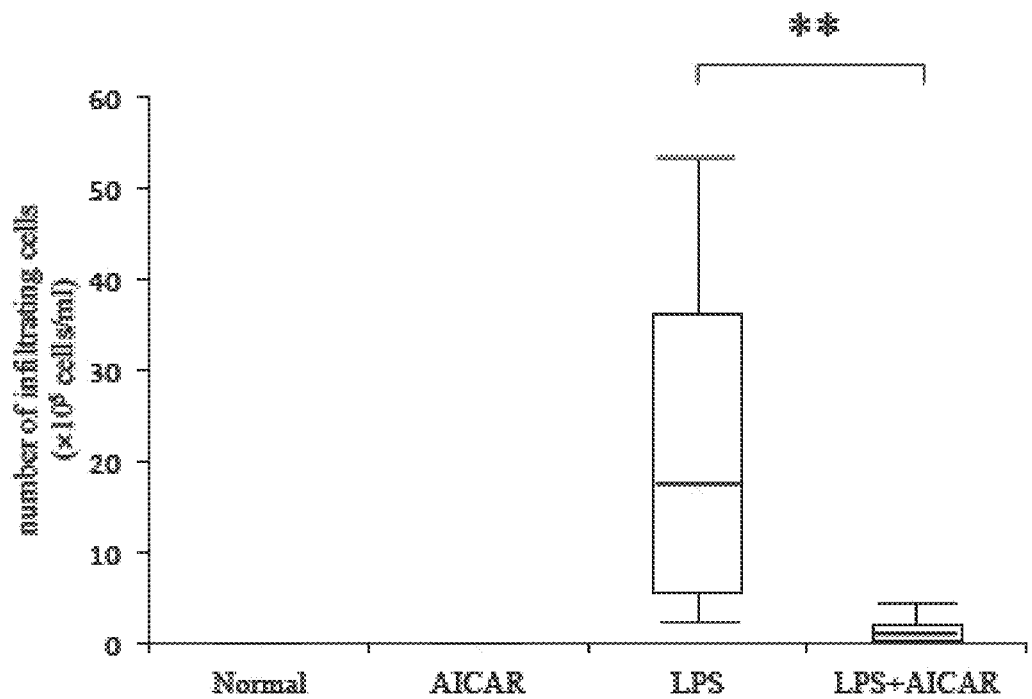
FIGS. 2A-2B depict the effect of AICAR on cellular infiltration and protein leakage in the aqueous humor.
Figure 2B:
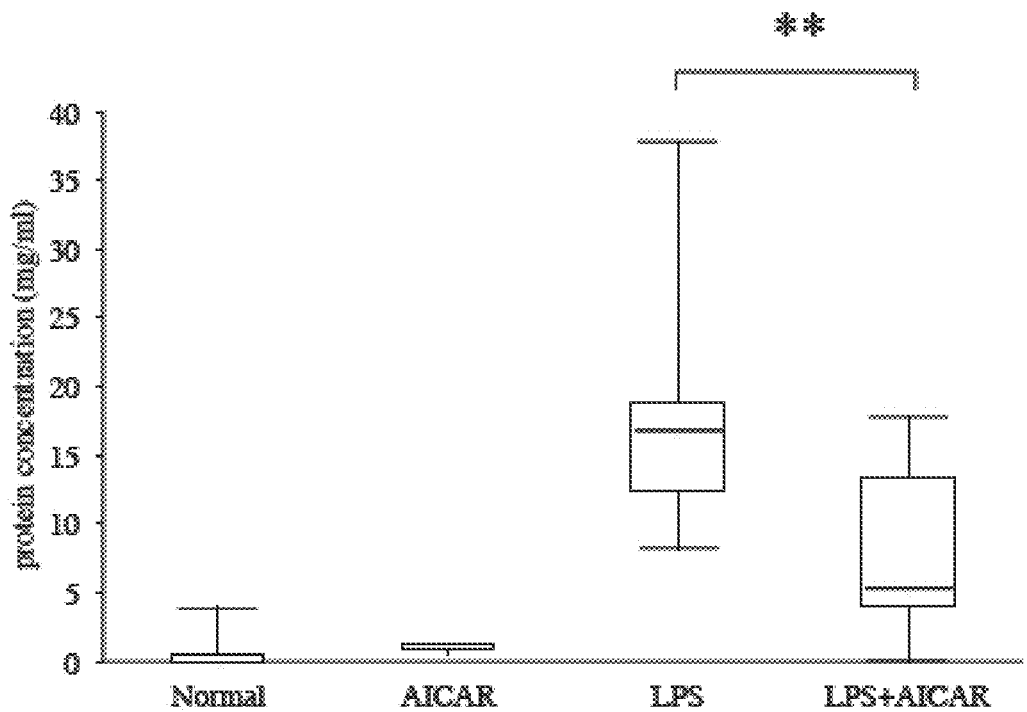

FIGS. 2A-2B depict the anti-inflammatory effect of AICAR on cellular infiltration and protein concentration in the aqueous humor. LPS injection induced severe cell infiltration into the aqueous humor ($22.0 \times 10^5$ cells/ml, range 2.5-53.0 cells/ml, n=11), whereas the number of infiltrating cells was reduced with AICAR pretreatment ($1.4 \times 10^5$ cells/ml, range 0-4.5 cells/ml, n=11, $p=0.001$). There was also an increase in total protein concentration in the aqueous humor of EIU rats (18.3 mg/ml, range 8.2-37.8 cells/ml, n=1), which was inhibited in AICAR-pretreated EIU rats (7.9 mg/ml, range 0-17.8 cells/ml, n=1, $p=0.006$). Normal control rats (n=6) and AICAR-only-treated rats (n=6) did not show any significant infiltration of cells nor a significant increase in protein levels in the aqueous humor.

These data indicate that AICAR treatment reduces cell infiltration into the aqueous humor.

Example 3: AICAR Treatment Suppresses Leukocyte Adhesion

Inflammation in the posterior segment of the eye is seen in EIU with the adherence of recruited leukocytes to the retinal vascular endothelium (Koizumi et al. (2003) INVEST. OPHTHALMOL. VIS. SCI. 44:2184-2191). Leukocyte adhesion to the retinal vessels was evaluated at 24 hours after EIU induction by using the Concanavalin A (Con A) lectin staining technique (Smith et al. (1994) INVEST. OPHTHALMOL. VIS. SCI. 35:101-111). After deep anesthesia, the chest cavities of rats were opened, and a 20-gauge perfusion cannula was introduced into the aorta. Rats were then perfused with 20 ml of PBS to remove erythrocytes and nonadherent leukocytes, followed by 20 ml of fluorescein-isothiocyanate (FITC)-coupled Con A (Vector Laboratories, Burlington, Calif.) in PBS for staining the vascular endothelium and firmly adherent leukocytes. Subsequently, residual unbound Con A was removed with 20 ml of PBS. The eyes were subsequently enucleated and the retinas were carefully flat-mounted. The flatmounts were imaged using an epifluorescence microscope (DM RXA; Leica) and the total number of Con A-stained adherent leukocytes per retina was counted.

Figure 3A:
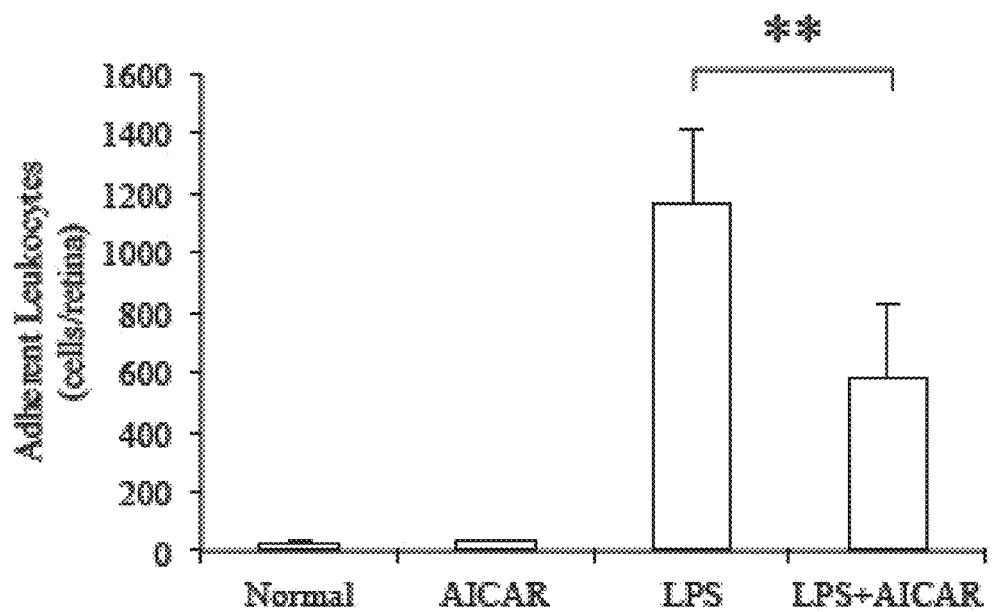
FIGS. 3A-3B depict the effect of AICAR on leukocyte adhesion in retinal vessels.
Figure 3B:
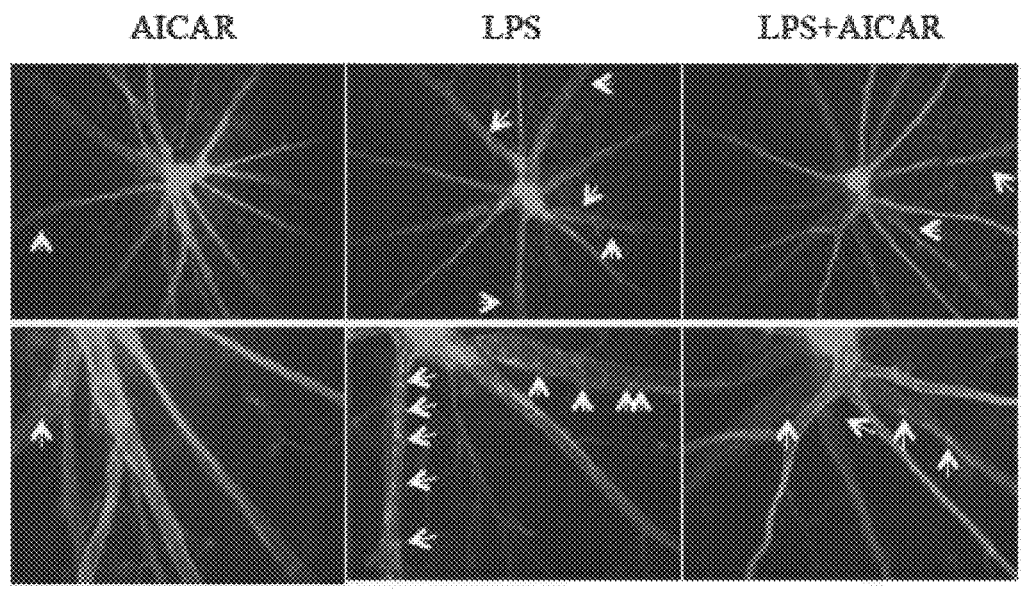

EIU-associated leukocyte adhesion to retinal vascular endothelium was reduced with AICAR pretreatment (FIGS. 3A and 3B). Normal control rats (n=5) and AICAR-only-treated rats (n=6) showed few adherent leukocytes. In contrast, EIU rats revealed significant numbers of adherent leukocytes at 24 hours after LPS injection (1163±244 cells, n=8). AICAR pretreatment of EIU rats resulted in significant suppression of leukocyte adhesion (576±249 cells, n=11, $p=0.001$).

Example 4: AICAR Treatment Suppresses Vascular Leakage

Protein leakage from retinal vessels was assessed with a biotinylated bovine serum albumin (bBSA) assay as previously described (Trichonas et al. (2010) INVEST. OPHTHALMOL. VIS. SCI. 51:1677-1682). At 23 hours after LPS injection, rats were anesthetized and 0.14 ml of 43.7 mg/ml bBSA (Santa-Cruz Biotechnology, Santa Cruz, Calif.) was injected through the femoral vein. After one hour, the chest cavities of rats were opened, and the rats were perfused with lactated Ringer's solution via the left ventricle for 6 minutes. Subsequently, the eyes were enucleated and retinas were carefully removed and placed in cold PBS. The retinas were then placed in 500 μl of lysis buffer containing protease inhibitor (Complete Protease Inhibitor Cocktail Tablets, Roche Diagnostics Corp, Indianapolis, Ind.), sonicated, and centrifuged at 13,000 rpm for 10 minutes. Supernatant was collected, and bBSA concentration was measured by enzyme-linked immunosorbent assay (ELISA). The degree of vascular leakage was estimated by measuring the protein concentration in each retina.

EIU rats had a higher amount of protein leakage from the retinal vessels as measured with bBSA assay (30.5±21.2 ng/mg total retinal protein, n=8) when compared to AICAR-pretreated EIU rats (11.2±7.2 ng/mg total retinal protein, n=8, $p=0.03$).

Example 5: AICAR Treatment Inhibits NF-κB Activity

To investigate the LPS-induced signal transduction pathway, NF-κB P65 protein levels translocated into the nuclei of retinal cell extracts were examined 3 hours after LPS injection. For the measurement of NF-κB activity, pooled retinas from six normal rats, nine EIU PBS-treated rats, and nine EIU AICAR-treated rats were analyzed. Retinas were homogenized and nuclear extracts were prepared with ProteoJet Cytoplasmic and Nuclear Protein Extraction Kit (Fermentas inc, Burlington, Canada). The amount of NF-κB in the nuclear extracts was analyzed by measuring the p65 protein levels with a NF-κB detection kit (p65 Transcription Factor Assay kit; Active Motif, Carlsbad, Calif.). NF-κB concentration was calculated and corrected for protein concentration.

Figure 4:
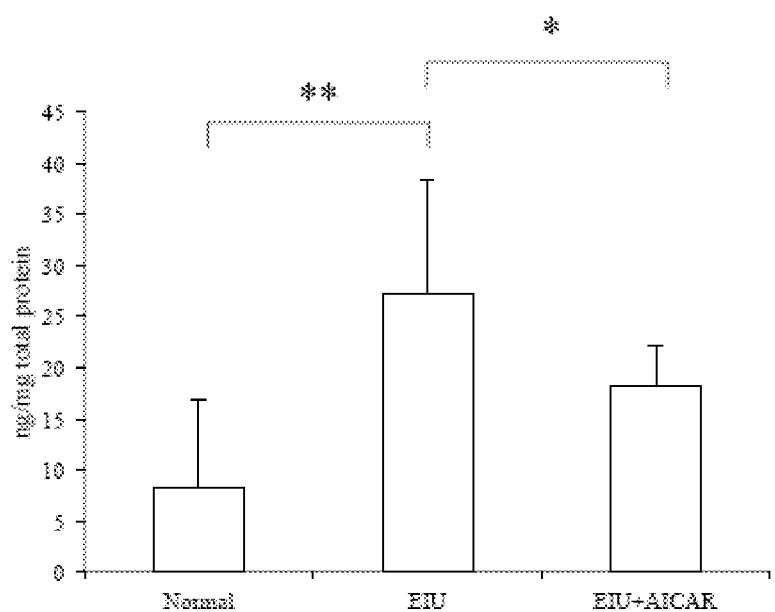
FIG. 4 depicts the effect of AICAR on NF-κB activity. NF-κB P65 levels in the retinal nuclear extract from normal control (n=6), LPS (n=9), LPS+AICAR (n=9) were determined by ELISA. Data are shown as mean±SD; *$p<0.05$, **$p<0.01$.

As shown in FIG. 4, protein levels in the nuclear extracts were significantly elevated in PBS-treated EIU rats (27.3±11.0 ng/mg total protein, n=9) compared to control rats (8.3±8.6 ng/mg total protein, n=6, p=0.004), whereas AICAR pretreatment significantly suppressed the upregulation (18.2±3.9 ng/mg total protein, n=9, p=0.03).

Stimulation by various signals, including exposure to LPS, lead to NF-κB activation and its movement into the nucleus where it triggers transcription of various pro-inflammatory genes including MCP-1, TNF-α and ICAM-1 (Baeuerle et al., (1994) ANNU REV IMMUNOL, 12:141-179; Baldwin et al., (1996) ANNU REV IMMUNOL, 14:649-683). In the retinal samples, LPS-induced NF-κB translocation to nuclei was significantly reduced in AICAR-pretreated rats. These results suggest that the subsequent diminished expression of inflammatory mediators in the eye could be the result of inhibition of NF-κB activity.

Example 6: AICAR Treatment Alters Intra-Ocular Cytokine and Chemokine Levels Under deep anesthesia, experimental rats were sacrificed and the retinas were carefully removed 24 hours after LPS injection, placed into 200 μl of lysis buffer and then sonicated. The lysate was centrifuged at 13,000 rpm for 10 minutes at 4° C. and supernatant was isolated. Three hours after LPS injection, blood samples were collected from the heart and subsequently centrifuged at 3000 rpm for 30 minutes at 4° C., and serum samples were separated. Cytokine and chemokine levels in the serum, aqueous humor, and retina were assessed using the rat CCL2/MCP-1 kit (Invitrogen, Camarillo, Calif.), the rat TNF-α kit (R&D system, Minneapolis, Minn.) and the rat ICAM-1 kit (R&D systems) by ELISA.

Protein expression of CCL2/MCP-1, TNF-α and ICAM-1 in the aqueous humor (n=12) and retina (n=14) were measured (Table 1). When compared to PBS-treated EIU rats, AICAR-pretreated EIU rats had significantly lower aqueous humor levels of CCL2/MCP-1 (p=0.005), TNF-α (p=0.002) and ICAM-1 (p=0.04). Similarly, expression of CCL2/MCP-1 and ICAM-1 in the retina was suppressed in the AICAR-pretreated group as compared to the PBS-treated group (p=0.004 and p=0.02, respectively). TNF-α protein was not detected in any retina.

Since AICAR was administered systemically, its suppressing effects on intraocular inflammation could have been mediated locally or systemically. To investigate the systemic effects of AICAR during EIU development, the serum cytokine levels at 3 hours after LPS injection (n=1) were also measured. Both CCL2/MCP-1 and ICAM-1 levels were suppressed in AICAR-pretreated EIU rats compared with PBS-treated rats (CCL2/MCP-1: 0.4±0.2 ng/ml vs 6.8±0.5 ng/ml, p=0.002 and ICAM-1: 21.6±5.0 ng/ml vs 28.7±8.1 ng/ml, p=0.02).

TABLE 1

Cytokine and chemokine production in aqueous humor, retina and serum

|  | LPS | LPS + AICAR | p value |
|---|---|---|---|
| Aqueous humor (n = 12) | | | |
| MCP-1 (ng/ml) | 4.4 ± 3.9 | 0.8 ± 1.0 | 0.005 |
| TNF-α (pg/ml) | 277.8 ± 123.9 | 92.5 ± 140.5 | 0.002 |
| ICAM-1 (ng/ml) | 8.7 ± 4.4 | 4.4 ± 3.3 | 0.037 |
| Retina (n = 14, pg/total retinal protein) | | | |
| MCP-1 | 18.7 ± 11.3 | 8.8 ± 2.9 | 0.004 |
| TNF-α | N.D. | N.D. | |
| ICAM-1 | 316.4 ± 132.3 | 202.9 ± 113.4 | 0.021 |
| Serum (n = 11) | | | |
| MCP-1 (ng/ml) | 6.8 ± 0.5 | 0.4 ± 0.2 | 0.002 |
| TNF-α (pg/ml) | 147.2 ± 337.1 | 57.8 ± 143.1 | 0.475 |
| ICAM-1 (ng/ml) | 28.7 ± 8.1 | 21.6 ± 5.0 | 0.023 |

N.D. = not detectable

Leukocyte adhesion to the retinal vessel is a well documented finding in EIU and expression of adhesion molecules such as ICAM-1 play a pivotal role in the pathogenesis of this finding (Yang et al. (2005) BLOOD 106:584-592). It has been previously noted that ICAM-1 is expressed on vascular endothelial cell of the iris and the ciliary body and that an antibody to ICAM-1 reduces ocular inflammation (Becker et al. (2001) INVEST. OPHTHALMOL. VIS. SCI. 42:2563-2566). As seen in Example 3, the number of adherent leukocytes in retinal vessels of EIU rats was reduced by AICAR pretreatment. It is contemplated that this may be explained at least in part by the observed reduction in retinal expression of ICAM-1 and MCP-1, which is also involved in leukocyte recruitment. Moreover, as seen in Example 4, retinal vascular impermeability was well maintained in the AICAR-pretreated rats. This can also be at least partially attributed to the reduced expression of inflammatory mediators observed in this study. These results suggest that AICAR could be effective for the posterior segment manifestation of inflammation, such as cystoid macular edema, which is a significant cause of vision loss in human uveitis.

Example 7: AICAR Treatment Suppresses CD14 Expression

CD14 is a co-receptor for LPS and expressed mainly on monocytes, macrophages and neutrophils, and its association with Toll-like receptor 4 leads to activation of transcriptional factors, including NF-κB (Takeda et al. (2003) ANNU. REV. IMMUNOL. 21:335-376). There have been reports that suppression of CD14 expression has a potent therapeutic effect on reducing LPS-induced inflammation including EIU (Sanchez-Lemus et al. (2009) AM. J. PHYSIOL. REGUL. INTEGR. COMP. PHYSIOL. 296:R1376-1384; Poulaki et al. (2007) FASEB. J. 21:2113-2123). Thus, the effects of AICAR treatment on CD14 mRNA and protein expression were assessed by real time PCR and Western Blot, respectively.

For preparation of peripheral blood mononuclear cell (PBMC) samples, blood samples were collected at three hours after LPS injection, and PBMC samples were isolated by density gradient centrifugation with Histopaque 1083 (Sigma). The red blood cells were lysed with Red Blood Cell Lysing Buffer (Sigma).

For Western blot analysis, pooled PBMCs from three rats were homogenized with lysis buffer (Roche Diagnostics Corp) and centrifuged at 13,000 rpm for 10 minutes at 4° C. Thirty μg of protein per sample was electrophoresed in a 4-20% gradient sodium dodecyl sulfate-polyacrylamide gel electrophoresis (SDS-PAGE) (Invitrogen) and electroblotted to polyvinylidene fluoride membrane (Millipore). After blocking with 5% skim milk, the membranes were incubated with a rabbit polyclonal antibody against CD14 (1:200, Santa Cruz Biotechnology) or GAPDH antibody (1:1000, Cell Signaling, Danvers, Mass.) at room temperature for one hour. The membranes were washed three times (five minutes each time) with TBS/Tween (TBST) and incubated for 30 minutes at room temperature with horseradish peroxidase-labeled anti-rabbit secondary antibody (1:20,000; Jackson ImmunoResearch, West Grove, Pa.). The membranes were then washed three times (five min each time) in TBST, and the proteins were visualized by ECL plus (GE Healthcare).

For measurement of CD14 mRNA expression by real time PCR, total RNA of PBMC was harvested from cells using the RNeasy kit (Qiagen, Valencia, Calif.), and complementary DNA (cDNA) was generated with the OligodT primer (Invitrogen) and Superscript II (Invitrogen) according to the manufacturer's instructions. Real-time PCR was carried out using the following TaqMan gene expression assays (Applied Biosystems): CD14 (Rn00572656_g1) and actin (Rn00667869_m1). Quantitative expression data were acquired and analyzed with a Step One Plus real-time PCR system (Applied Biosystems).

Figure 5A:
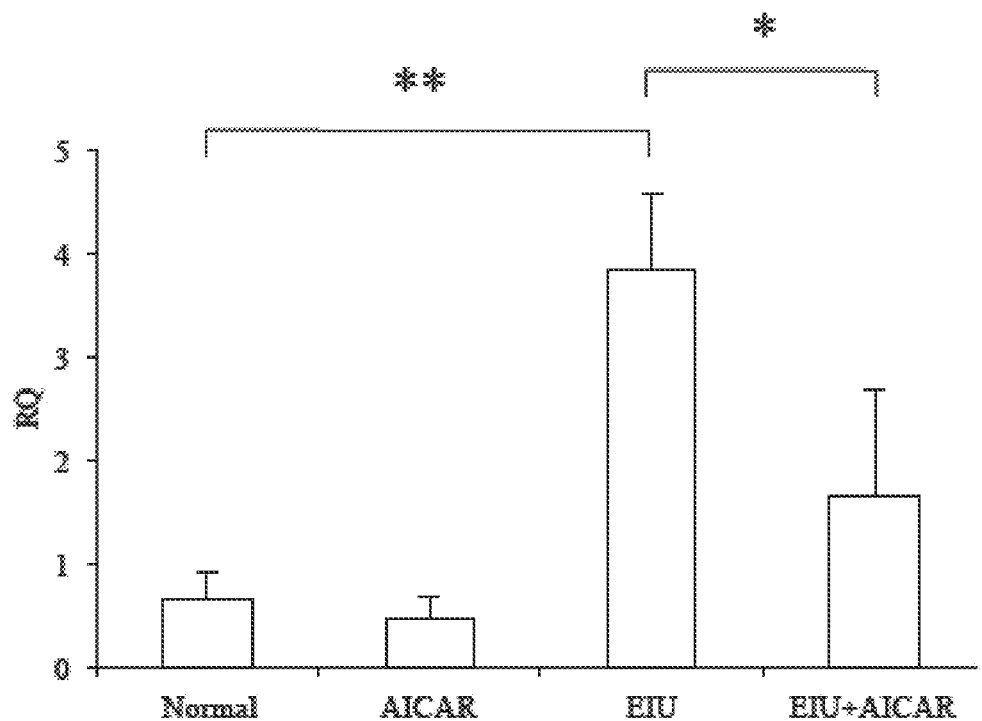
FIGS. 5A-5B depict the effect of AICAR on CD14 expression.
Figure 5B:
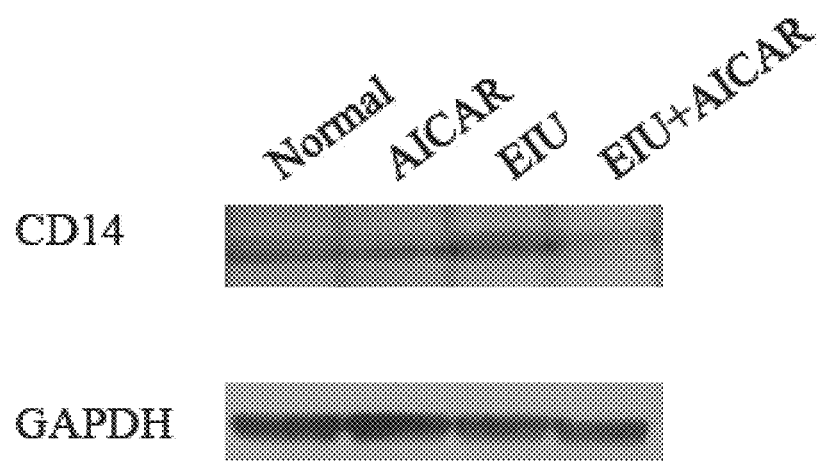

As depicted in FIGS. 5A and 5B, at three hours after LPS injection, CD14 mRNA expression in PBMCs from EIU rats was significantly increased (3.8±0.7, n=9) compared to normal rats (0.7±0.3, n=6, p=0.009). AICAR pretreatment significantly suppressed CD14 mRNA levels (1.7±1.0, n=9, p=0.03). Similarly, protein expression of CD14 was increased in EIU rats but decreased in AICAR-pretreated rats.

Collectively, these results demonstrate that both protein and mRNA expression of CD14 were increased after LPS stimulation and pretreatment with AICAR significantly suppressed these elevations. It has been reported that LPS stimulation decreases AMPK activity in macrophages and increases their production of inflammatory cytokines, while AICAR may upregulate AMPK activity and suppress cytokine production. It is contemplated that one of the treatment effects of AICAR is to decrease LPS susceptibility by suppressing CD14 expression.

Example 8: AICAR Treatment Suppresses Uveitis in Experimental Autoimmune Uveitis (EAU)

The ability of AICAR to suppress autoimmune-mediated intraocular inflammation was investigated in a model of experimental autoimmune uveitis (EAU). EAU is a rodent model of human autoimmune uveitis and has been used for studying the mechanism of autoimmune uveitis and for developing therapeutic strategies (Luger et al. (2008) SEMIN. IMMUNOPATHOL. 30:135-143). In this model, EAU is induced by immunizing mice with retinal antigens such as interphotoreceptor retinoid-binding protein (IRBP) (Rizzo et al. (1996) J. IMMUNOL. 156:1654-1660; Sanui et al. (1989) J. EXP. MED. 169:1947-1960).

Female C57BL/6 (WT) mice ranging from 6-8 weeks old (Charles River, Wilmington, Mass.) were used for these studies.

To induce EAU, WT mice were immunized subcutaneously with 200 μg of human interphotoreceptor retinoid-binding protein (hIRBP) 1-20 (GPTHLFQPSLVLDMAKV-LLD) (SEQ ID NO:1) (Biomatik, Wilmington, Del.) emulsified in CFA (1:1 v/v) containing 2.5 mg/ml *M. tuberculosis* (Difco, Detroit, Mich.). As an additional adjuvant, 0.1 g of purified *Bordetella pertussis* toxin (PTX, Sigma, St. Louis, Mo.) was also injected intraperitoneally. To study the effect of AICAR on EAU, AICAR (100 or 200 mg/kg body weight, Toronto Research Chemicals, Ontario, Canada) was diluted in 0.15 ml phosphate-buffered saline (PBS) and administered daily via intraperitoneal injection from day 0 to 21 after immunization. Control animals were injected with PBS.

Clinical scoring of EAU was performed by funduscopic examination in a masked fashion as previously described (Pouvreau et al. (1998) J. NEUROIMMUNOL. 86:171-181). On day 21 after immunization, vascular dilation, white focal vascular lesions, white linear vascular lesions, retinal hemorrhage and retinal detachment were evaluated and the severity of EAU was graded on scale of 0-4 as described by Thurau et al. (1997) CLIN. EXP. IMMUNOL. 109:370-376. For histological assessment, eyes were enucleated on day 21 and immediately frozen in optimal cutting temperature compound (Sakura Finetek, Torrance, Calif.). Ten μm-thick sections were cut near the optic nerve head, air-dried, and fixed in 4% paraformaldehyde and stained with hematoxylin and eosin. The severity of EAU in each eye was scored on a scale of 0-4 based on the number, type, and size of lesions as previously described (Caspri et al. (1988) J. IMMUNOL. 140:1490-1495).

Figure 6A:
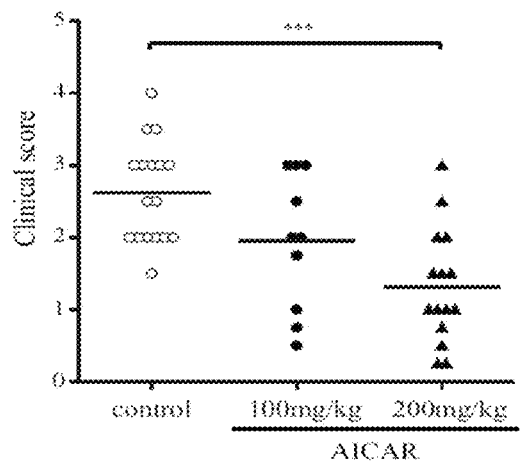
FIGS. 6A-6F depict the effect of AICAR on experimental autoimmune uveitis (EAU).
Figure 6B:
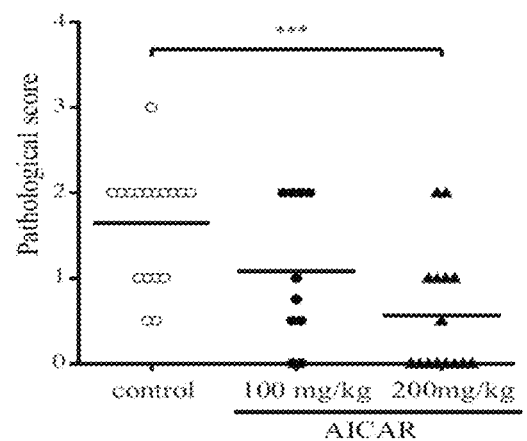
Figure 6C:
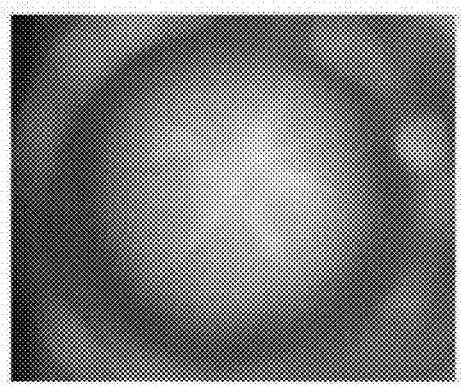
Figure 6D:
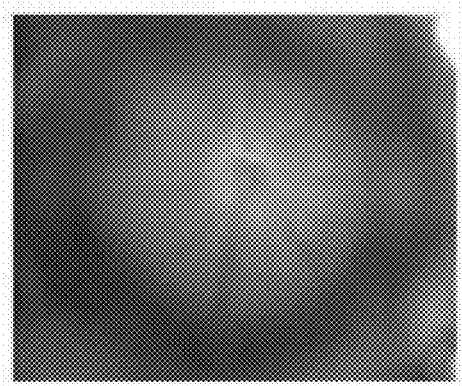
Figure 6E:
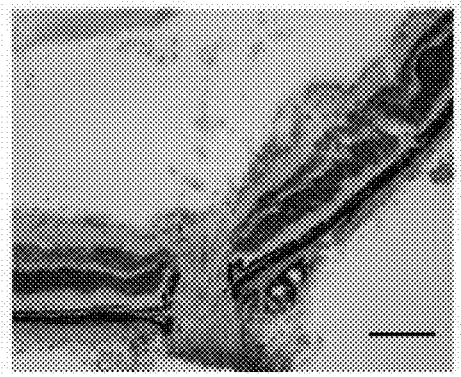
Figure 6F:
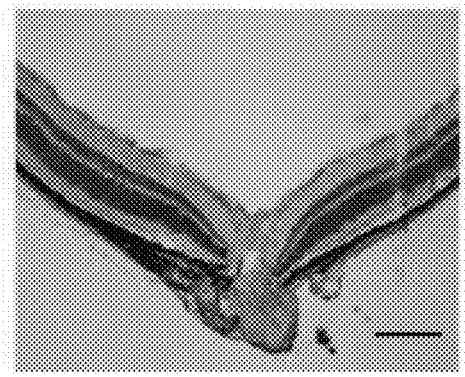

As depicted in FIGS. 6A, 6C and 6D, fundus examination showed that AICAR treatment suppressed clinical inflammation in a dose-dependent manner. More specifically, mean clinical scores were significantly reduced in mice treated with 200 mg/kg of AICAR (1.32±0.95, n=15, p=0.0002) when compared with the control animals (2.6±0.70, n=17). Histological examination also confirmed the ability of AICAR to suppress ocular inflammation. As shown in FIGS. 6B, 6E and 6F, mean pathologic scores were reduced in mice treated with 200 mg/kg of AICAR (0.53±0.73, p=0.0008) when compared to control mice (1.65±0.68, p=0.0008). Since 200 mg/kg of AICAR showed the most robust results compared to controls, all other experiments using the EAU model were conducted with this dose.

Altogether, these data indicate that AICAR administration has an anti-inflammatory effect on EAU as demonstrated by clinical and histological findings.

Example 9: AICAR Suppresses Intraocular Inflammation

To investigate the effect of AICAR on retinal inflammation, the mRNA and protein levels of various inflammatory cytokines were assessed. Total RNA from the retina was harvested using the RNeasy kit (Qiagen, Valencia, Calif.). Complementary DNA (cDNA) was generated with OligodT primer (Invitrogen, Camarillo, Calif.) and Superscript II (Invitrogen) according to manufacturer's instructions. Real-time PCR was carried out using the following TaqMan gene expression assays (Applied Biosystems, Foster City, Calif.): IL-6 (Mm99999064_m1), IFN-γ (Mm01168134_m1), TNF (Mm99999068_m1), and actin (Mm00607939_s1). Quantitative expression data were acquired and analyzed with a Step One Plus real-time PCR system (Applied Biosystems).

For the retinal cytokine analysis, 8 to 10 retinas were removed 21 days after immunization and placed into 500 μl of lysis buffer (Complete Protease Inhibitor Cocktail Tablets, Roche Diagnostics Corp, Indianapolis, Ind.) containing protease inhibitor. After sonication, the lysate was centrifuged at 13,000 rpm for 10 minutes at 4° C. and supernatant was collected. Cytokine levels were measured by ELISA using the Quantikine mouse IFN-γ, IL-6 and TNF-α kits (R&D system, Minneapolis, Minn.). The amount of cytokine present was normalized to total protein concentration in each retina.

Figure 7A:
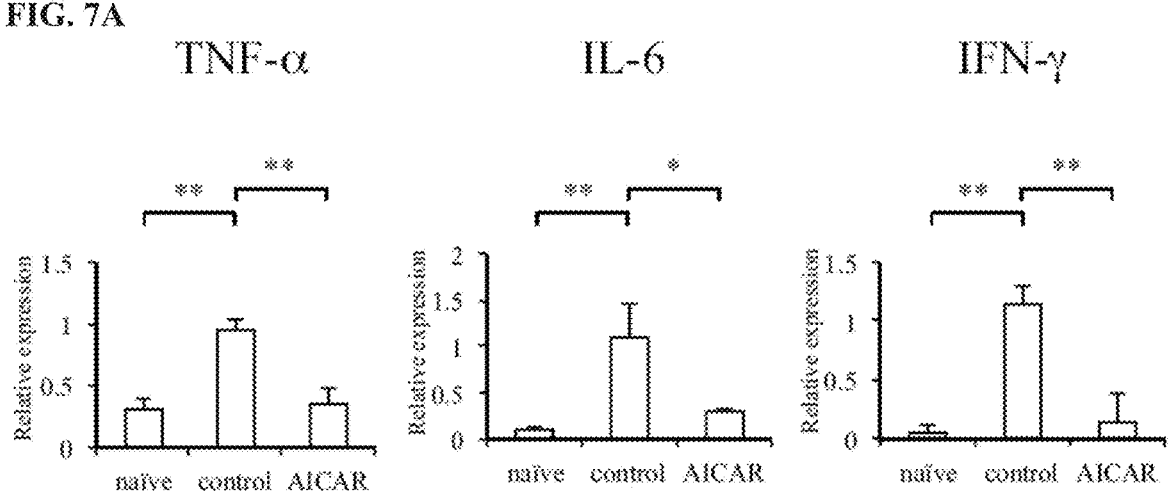
FIGS. 7A-7B depict the effect of AICAR on retinal inflammation.
Figure 7B:
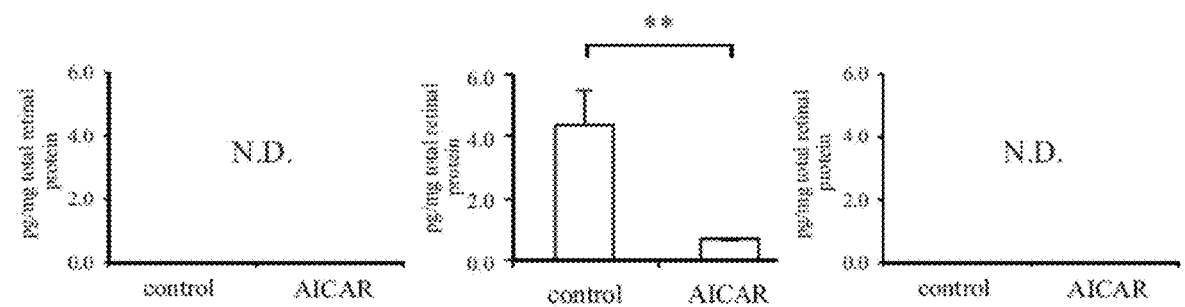

As shown in FIG. 7A, EAU (i.e., control) mice showed elevated levels of TNF-α, IL-6 and IFN-γ mRNA when compared to wildtype (i.e., naïve) mice. AICAR treatment significantly reduced the levels of TNF-α, IL-6 and IFN-γ mRNA. As shown in FIG. 7B, AICAR treatment also suppressed the protein levels of IL-6 when compared to naive and control mice. Together these data indicate that AICAR suppresses intraocular inflammatory cytokine production and retinal inflammation.

Example 10: AICAR Suppresses Proliferation and Cytokine Production by Lymph Node (LN) Cells In the EAU model, activated and sensitized Th1 and Th17 cells are considered to play a major role in the initiation and maintenance of intraocular inflammation (Yoshimura et al. (2008) INT. IMMUNOL. 20:209-214; Amadi-Obi et al. (2007) NAT. MED. 13:711-718). Specifically, Th1 and Th17 cells respond to retinal antigen resulting in intraocular inflammation, posterior uveitis, disc edema, retinal exudates, vasculitis, and retinal detachment (Luger et al. (2008) SEMIN. IMMUNOPATHOL. 30:135-143; Caspi (2008) IMMUNOL. RES. 42:41-50). Thus, to determine the mechanism by which AICAR suppresses intraocular inflammation and uveitis, the effect of AICAR on T cell response was investigated. More specifically, IRBP-specific T cell responses and cytokine profiles were examined in lymph node (LN) cells.

To extract LN cells, draining lymph nodes from 6 to 8 mice were isolated at sixteen days after immunization and pooled. Single cell suspensions were made using a cell strainer (BD, Franklin Lakes, N.J.). CD4 T cell-enriched fractions were prepared using CD4 Microbeads (Miltenyi Biotec GmbH, Bergisch Gladbach, Germany), and purity of the suspensions was determined by staining with anti-CD4 antibody (GK1.5, Biolegend, San Diego, Calif.) and flow cytometry. All experimental samples of CD4 T cell-enriched fractions were at least 95% CD4-positive.

To measure cell proliferation, LN cells were resuspended at $5 \times 10^5$ cells per 200 μl of medium in 96-well flat-bottom plates. Cells were incubated for 72 hours and proliferation during the last 12 hours was measured by using a bromodeoxyuridine (BrdU) cell proliferation assay kit (Millipore, Billerica, Mass.). Supernatant in the culture medium was collected at 48 hours and cytokine production in the supernatant was measured by ELISA using the Quantikine mouse IFN-γ, IL-4, IL-10 and IL-17 kits (R&D system, Minneapolis, Minn.).

To measure the expression of T-bet and RORγt, real-time PCR was carried out as described above using the following TaqMan gene expression assays: T-bet (Mm00450960_m1) and RORγt (Mm01261022_m1). Quantitative expression data were acquired and analyzed with a Step One Plus real-time PCR system (Applied Biosystems).

Figure 8A:
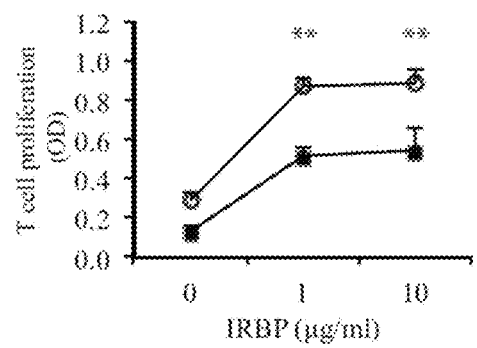
FIGS. 8A-8H depict the effect of AICAR on the development of IRBP-reactive T cells in vivo. Lymph node (LN) cells from control (open circles) and AICAR-treated mice (closed squares) were stimulated with IRBP (FIG. 8A) and anti-CD3 (FIG. 8B). Proliferative response was measured with BrdU incorporation.
Figure 8B:
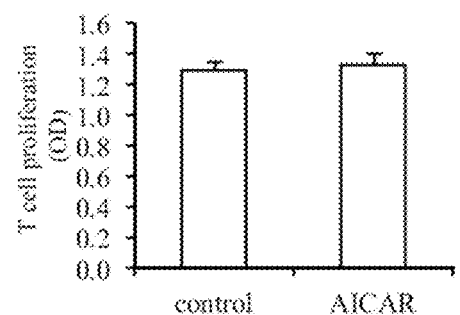
Figure 8C:
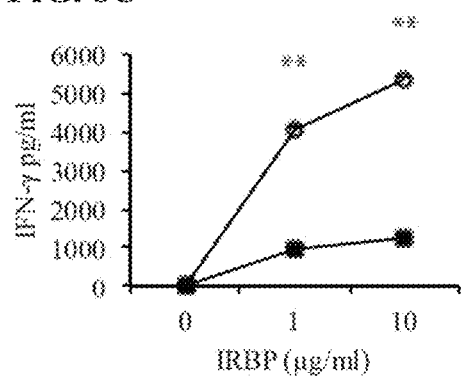
Figure 8D:
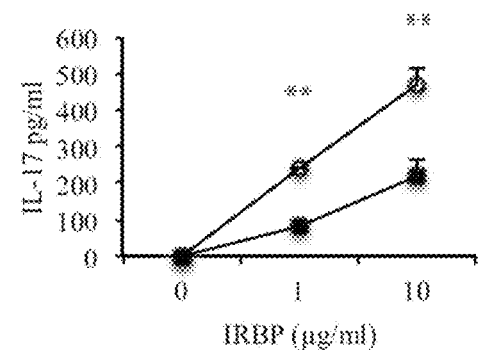
Figure 8E:
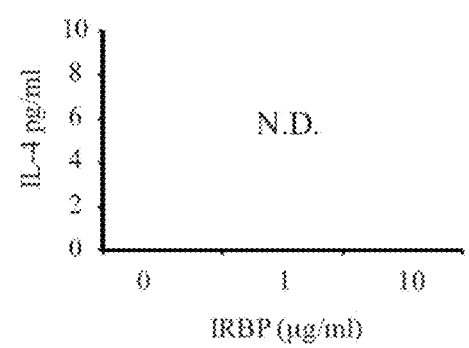
Figure 8F:
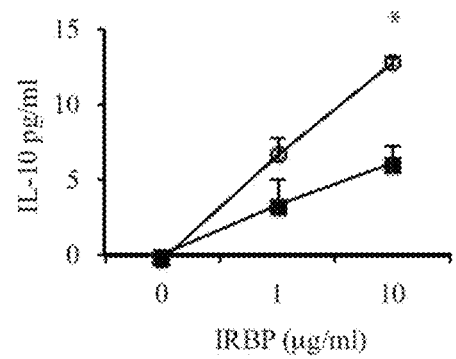

In order to assess the in vivo effect of AICAR on the development of IRBP-reactive T cells, LN cells from control and AICAR-treated mice were stimulated with either IRBP or a non-specific T cell stimulator, anti-CD3. Proliferative response was measured with BrdU incorporation. As shown in FIG. 8A, AICAR treatment suppressed antigen-specific T cell proliferation in a dose-dependent manner when compared to untreated mice. In comparison, when the cells were treated with anti-CD3, there was no difference in T cell proliferation between the AICAR treated and control mice (FIG. 8B).

Figure 8G:
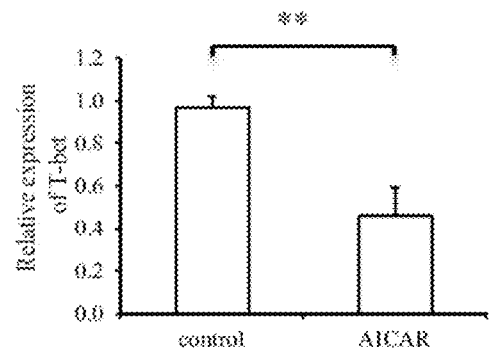
Figure 8H:
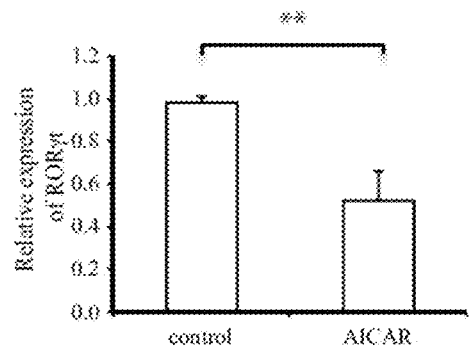

As shown in FIGS. 8C-8F, AICAR significantly suppressed the production of IFN-γ, IL-17, and IL-10 by LN cells. Further, AICAR treatment also suppressed the expressions of T-bet and RoRγt, which are transcription factors for Th1 and Th17 cells (FIGS. 8G and 8H, respectively).

Together, these results suggest that AICAR suppresses Th1 and Th17 cell proliferation and cytokine production.

Example 11: Effect of AICAR on Fox-P3 Expression (Treg) on LN Cells

In the EAU model, it was previously demonstrated that a shift towards a Th2 response and an increase in the Treg population and in regulatory cytokine production occur as a result of Th1 and Th17 cell suppression (Sun et al. (2010) INVEST. OPTHALMOL. VIS. SCI. 51:383-389; Keino et al. (2007) BR. J. OPTHALMOL. 91:105-110). It has been further reported that the Th2 response is related to the resolution of EAU (Takeuchi et al. (2001) JPN. J. OPTHALMOL. 45:463-469) and that this response increases in AICAR-treated experimental autoimmune encephalomyelitis mice during the late phase (Nath et al. (2005) J. IMMUNOL. 175:566-574).

In the current EAU model, a Th2 response was not detected during the inflammatory stage and could not be induced by in vitro treatment with AICAR. Further, as was shown in Example 10, AICAR suppressed the production of IL-10, which is a regulatory cytokine produced by Type-1 T regulatory (Tr1) cell (Pot et al. (2011) SEMIN. IMMUNOL. 23:202-208) and Treg cells.

Figure 9:
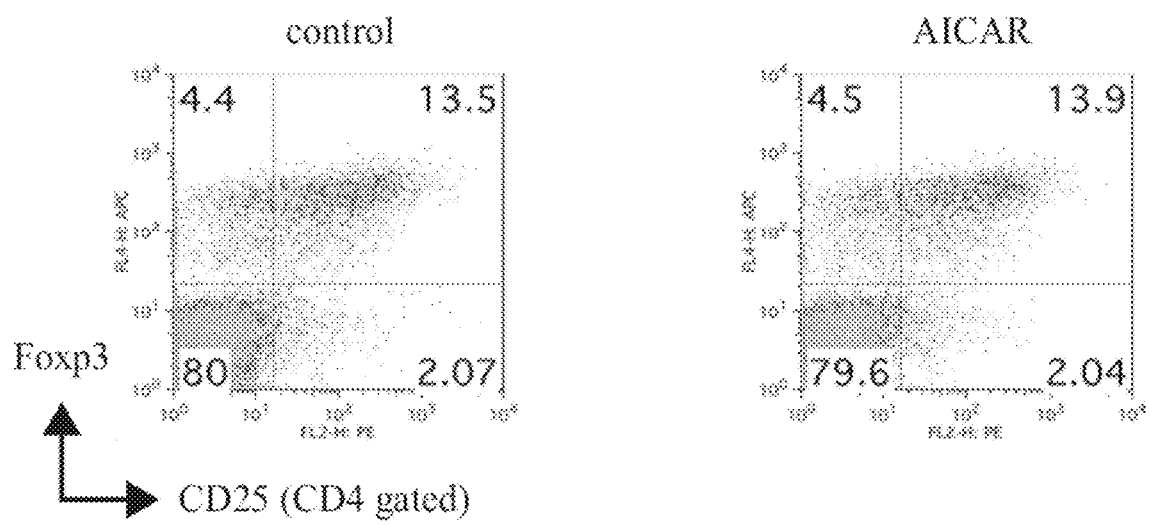
FIG. 9 depicts the effect of AICAR on the $T_{reg}$ population. LN cells from controls and AICAR-treated mice were collected at 21 days after immunization (n=5). The number of FoxP3$^+$CD25$^+$CD4$^+$ T cells was analyzed by fluorescence-activated cell sorting (FACS). Data are representative of two independent experiments.

The effect of AICAR on the regulatory T (Treg) cell population in the EAU mice was also directly assessed. Specifically, LN cells from five mice were harvested at 21 days after immunization and stained with a mouse regulatory T cell staining kit #2 (eBioscience) according to manufacturer's instructions. $CD4^+CD25^+Foxp3^+$ Treg populations were subsequently detected by flow cytometry. As shown in FIG. 9, the $CD4^+CD25^+Foxp3^+$ Treg population was not significantly different between control and AICAR-treated mice. These results suggest that AICAR may mediate its effects independent of any effects on Th2, Tr1 and Treg cells.

Example 12: AICAR Suppressed EAU During the Effector Phase

To examine whether AICAR might have an effect on the effector phase of EAU, AICAR or PBS were administered from day 8 to 21 after immunization. Both clinical and histopathological findings revealed that AICAR treatment administered during the effector phase significantly suppressed EAU (mean clinical score: 2.44±0.56 in controls vs. 1.50±0.86 in AICAR-treated mice, p=0.031; mean pathologic score: 1.03±0.75 in controls vs. 0.13±0.27 in AICAR-treated mice, p=0.004, n=8).

To assess the effect of AICAR on already developed IRBP-specific T cells, LN cells from untreated EAU mice were cultured with IRBP peptide in the presence of AICAR (FIGS. 10A-10E). Specifically, LN cells were resuspended at 5×10⁵ cells per 200 μl of medium in 96-well flat-bottom plates. Triplicate samples of cells were stimulated with or without IRBP at the indicated concentrations. AICAR was added at the indicated concentrations. Cell proliferation and cytokine production were measured as previously described in Example 10.

Figure 10A:
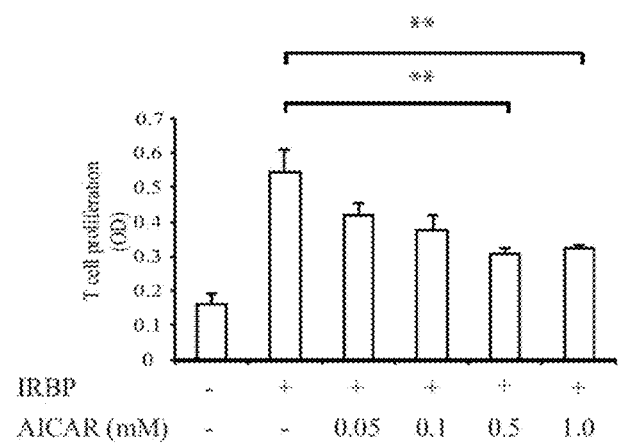
FIGS. 10A-10E depict the effect of AICAR on IRBP-reactive T cells in vitro. LN cells from untreated EAU mice (day 14) were cultured with or without AICAR in the presence of IRBP. Proliferative response (FIG. 10A) and production of IFN-γ (FIG. 10B), IL-17 (FIG. 10C), IL-4 (FIG. 10D) and IL-10 (FIG. 10E) were measured. Data are expressed as mean±SD and representative of three independent experiments. **$p<0.01$.
Figure 10B:
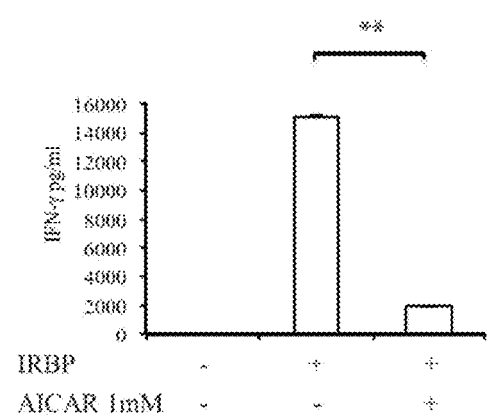
Figure 10C:
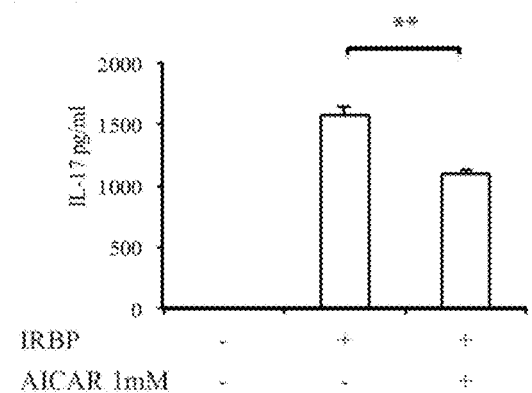
Figure 10D:
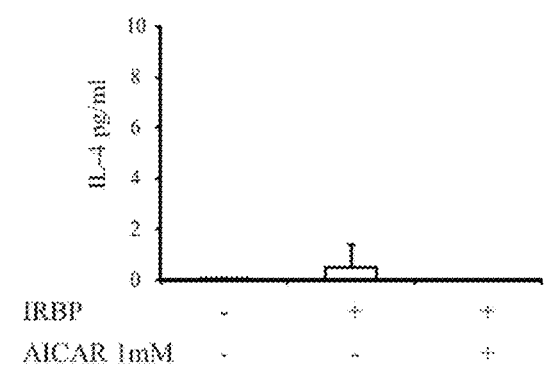
Figure 10E:
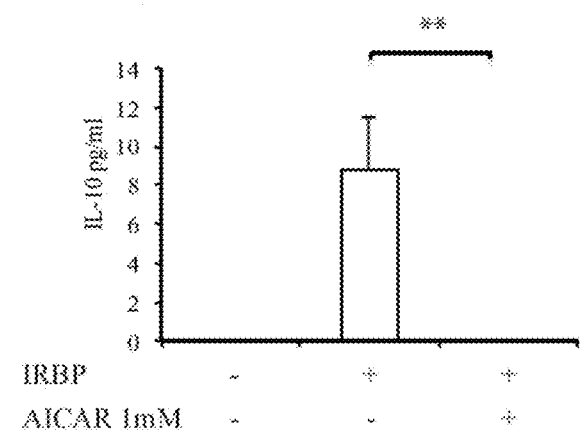

As shown in FIGS. 10A-10C and 10E, in vitro treatment with AICAR suppressed T cell proliferation and IFN-γ, IL-17 and IL-10 production. IL-4 production was not significantly induced (FIG. 10D).

Given that AICAR suppressed inflammation and T cell proliferation as well as cytokine production during the effector phase of EAU, it is contemplated that AICAR may be effective in treating ongoing human uveitis.

Example 13: AICAR Affects Dendritic Cell (DC) Phenotype

It is contemplated that AICAR may impair the interaction between T cells and antigen presenting cells (APCs), more specifically, dendritic cells (DCs) which are known as professional APCs. It has been reported that AMPK negatively regulates DC maturation by affecting their energy production pathway (Krawczyk et al. (2010) BLOOD 115:4742-4749). Further, it is know that co-stimulatory signals are involved in the course of EAU and blockade of these signals ameliorates intraocular inflammation (Bagenstose et al. (2005) J. IMMUNOL. 175:124-130; Namba et al. (2000) J. IMMUNOL. 165:2962-2969; Fukai et al. (1999) GRAEFES. ARCH. CLIN. EXP. OPTHALMOL. 237:928-933). For antigen specific T cell proliferation, naive CD4 T cells interacts with antigen presenting cells (APC) which express co-stimulatory molecules (second signals) such as CD40, CD80 and CD86 in addition to MHC molecules (first signals) (Jenkins (1994) IMMUNITY 1:443-446; Janeway et al. (1994) CELL 76:275-285).

To investigate whether DC maturation was affected by AICAR, splenic DCs were isolated from EAU mice and analyzed for co-stimulatory molecule expression. Specifically, spleen cells from 4 to 5 EAU mice were pooled at twelve days after immunization and incubated with the following monoclonal antibodies: anti-CD11c (N418), CD40 (3/23), CD80 (16-10A1), CD86 (GL-1), I-A$^b$ (AF6-120.1) (Biolegend). Spleen cells were gated on the basis of forward and side scatter profile and propidium iodide or DAPI exclusion. Samples of 1×10⁶ cells were analyzed by LSR (Becton Dickinson, Franklin Lakes, N.J.).

Figure 11:
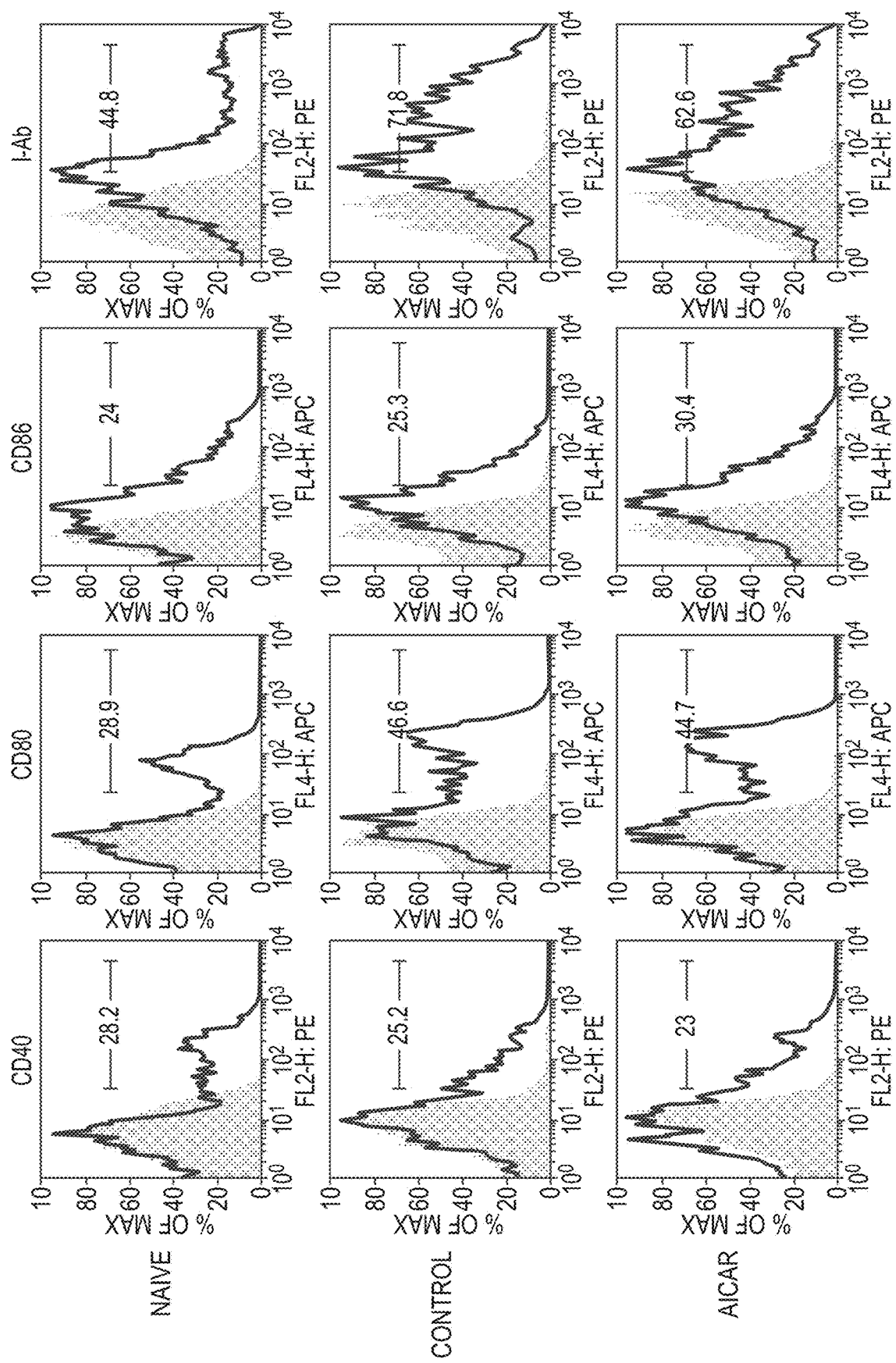
FIG. 11 depicts the effect of AICAR on dendritic cell (DC) maturation in vivo. Spleen cells from naive, control EAU and AICAR-treated EAU mice (n=4 to 5 for each group) were separated. The number of CD11c-gated CD40, CD80, CD86 and I-A$^b$ positive cells were examined by FACS. Data are representative of two independent experiments.

As indicated in FIG. 11, the expression of CD80 and I-Ab was elevated whereas CD40 and CD86 were not changed after IRBP immunization. There was no difference between the AICAR-treated and non-treated groups, which may be due to the heterogeneity of the DC population in vivo. Thus, experiments using in vitro cultured bone marrow-derived DCs (BMDCS) were performed to examine the potential role of AICAR on DC maturation.

Figure 12A:
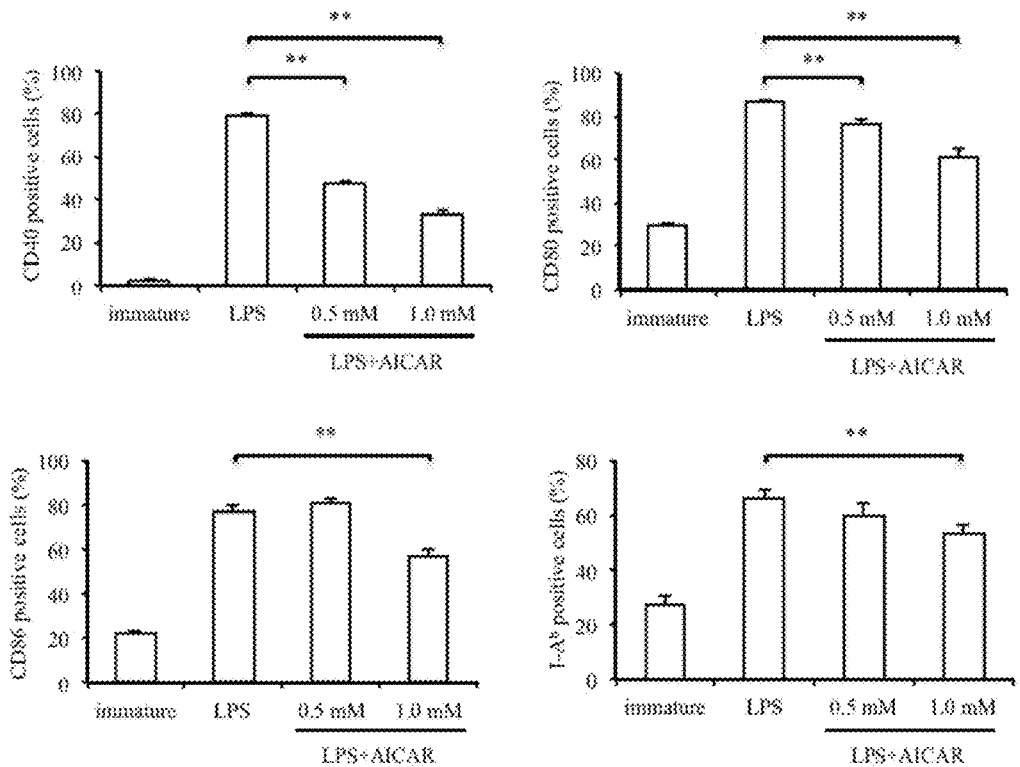
FIGS. 12A-12B depict the effect of AICAR on bone marrow derived dendritic cell (BMDC) maturation. Immature BMDCs were stimulated with LPS for 24 hours in the presence or absence of AICAR.

BMDCs were generated as previously described (Wang et al. (2005) IMMUNOL. LETT. 98:123-130). Briefly, bone marrow was flushed from the femurs and tibias of naive mice (6 to 8-week-old WT or AMPKα1 KO mice). The red blood cells were lysed using Red Blood Cell Lysing Buffer (Sigma). Approximately 2×10⁶ cells were cultured in complete medium (RPMI 1640 medium containing 10% FBS, 50 mM 2-ME, 10 mM HEPES [pH 7.4], 2 mM glutamine, 100 U/ml penicillin, and 100 mg/ml streptomycin) including 10 ng/ml GM-CSF (Pepro Tech, London, England). Fresh media was added to the cells on day 4 of culture, and nonadherent cells and loosely adherent cells were collected as immature DCs on day 7. Immature DCs were stimulated with 100 ng/ml LPS (*Salmonella typhimurium*; Sigma) for 24 hours to obtain mature DCs. In some experiments, AICAR was added to the culture. As shown in FIG. 12A, the expressions of CD40, CD80, CD86 and I-A$^b$ were markedly elevated after stimulation of BMDCs with LPS. AICAR significantly suppressed these elevations in a dose-dependent manner.

Figure 12B:
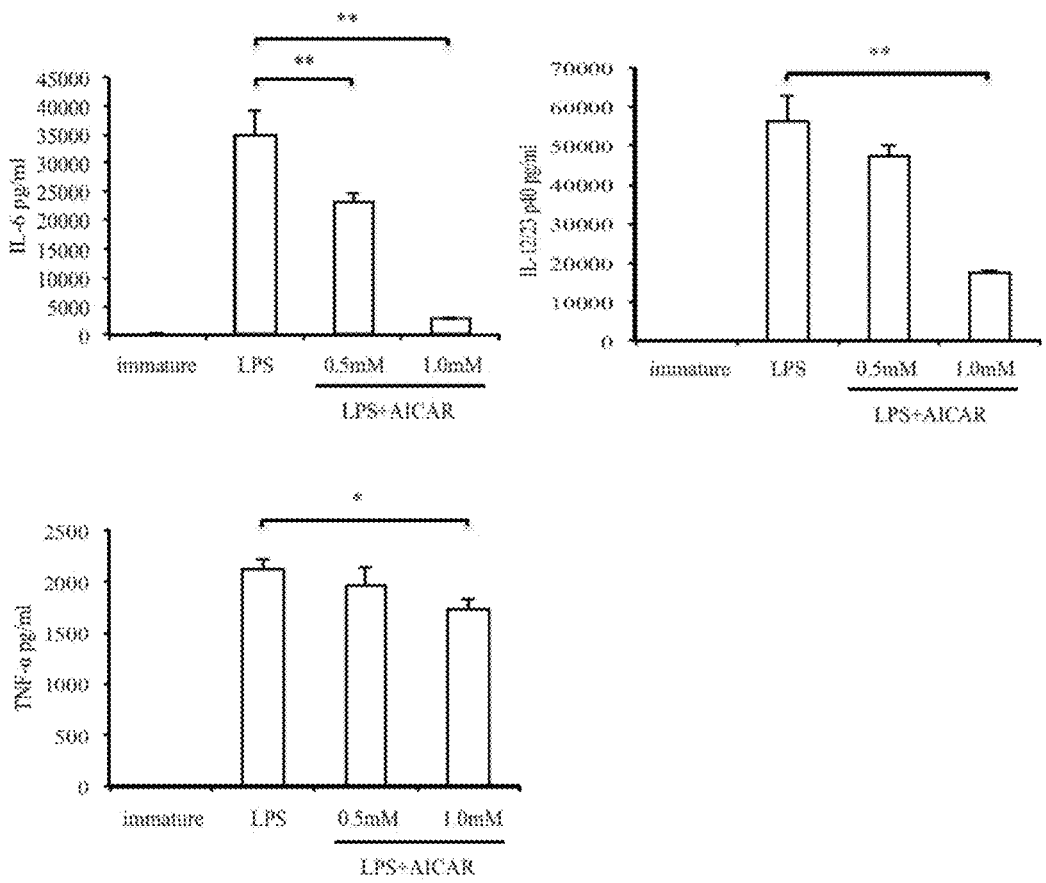

After LPS stimulation for 24 hours, supernatant of the BMDC culture was collected and IL-6, TNF-α and IL12/23 p40 concentrations were measured (R&D system). As indicated in FIG. 12B, AICAR significantly suppressed the production of IL-6, IL-12/23 p40 and TNF-α in BMDCs.

Altogether, these data suggest that at least part of the effect of AICAR in EAU is mediated through its effect on DC maturation and subsequent T cell proliferation and differentiation.

Example 14: AICAR Affects DC Maturation and AMPK

In these experiments, AMPKα1 KO mice were provided as previously described (Jorgensen et al. (2004) J. BIOL. CHEM. 279:1070-1079).

AICAR is a cell permeable activator of AMP-activated protein kinase (AMPK), which is a Serine/Threonine kinase that senses cellular energy status. Once inside the cell, AICAR is phosphorylated by adenosine kinase to the monophosphorylated form (ZMP), which mimics AMP and activates AMPK. AMPK is also implicated in the inflammatory response. Activation of AMPK changes macrophage function to an anti-inflammatory phenotype (Sag et al. (2008) J. IMMUNOL. 181:8633-8641) and inhibits dendritic cell (DC) maturation (Krawczyk et al. (2010) BLOOD 155:4742-4749), which is essential to induce lymphocyte activation.

Figure 13:
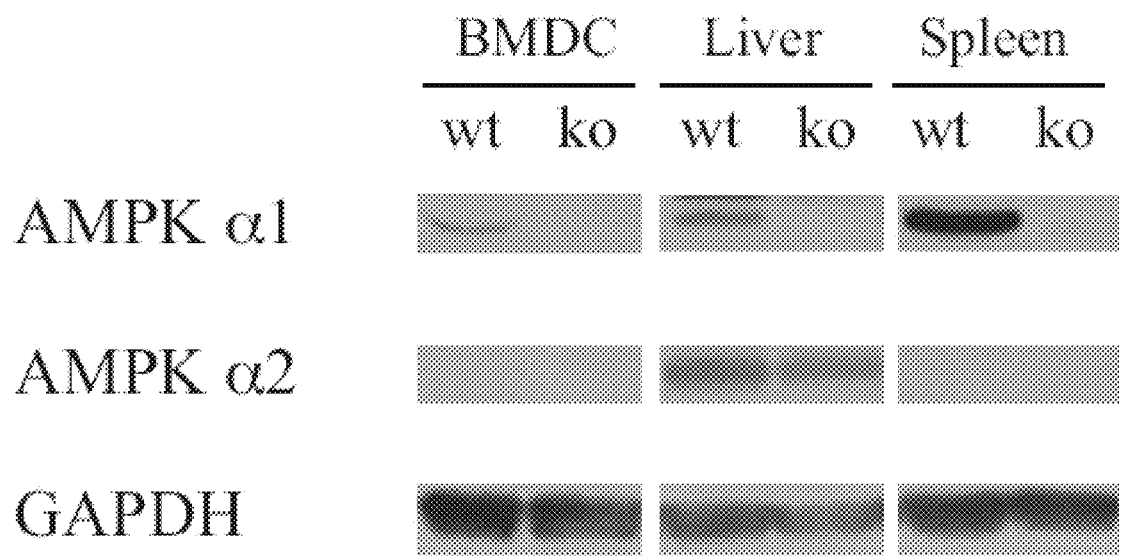
FIG. 13 depicts western blots showing AMPK expression in WT and AMPKα1 KO mice. Lysates of BMDC, liver and spleen were analyzed by Western blot using antibodies against AMPKα1 and α2. WT BMDCs only express AMPKα1. AMPKα1KO BMDCs do not express detectable amounts of AMPK.

AMPK is a heterotrimeric complex and the catalytic subunits of AMPKα consists of α1 and α2 and regulatory β and γ subunits (Hardy et al. (2003) FEBS LETT. 546:113-120). Western blot analysis was performed to determine the AMPKα1 and AMPKα2 expression in mice. Specifically, 20 μg of lysate from BMDC, liver and spleen of WT and AMPKα1 KO mice were electrophoresed in a 4-20% gradient sodium dodecyl sulfate-polyacrylamide gel electrophoresis (SDS-PAGE) (Invitrogen) and electroblotted to polyvinylidene fluoride membrane (Millipore). After blocking with blocking buffer (Thermo scientific, Rockford, Ill.), the membranes were incubated with a rabbit polyclonal antibody against AMPKα1, AMPKα2 (1:1000, Abcam, Cambridge, Mass.) or GAPDH antibody (1:1000, Cell Signaling, Danvers, Mass.). The membranes were washed three times (5 minutes each time) with TBS/tween (TBST) and incubated for 30 minutes at room temperature with horseradish peroxidase-labeled anti-rabbit secondary antibody (1:20,000; Jackson ImmunoResearch, West Grove, Pa.). The membranes were washed again three times (5 minutes each time) in TBST, and the proteins were visualized by ECL plus (GE Healthcare, Piscataway, N.J.). As shown in FIG. 13, BMDCs expressed only the AMPKα1 subunit.

Figure 14A:
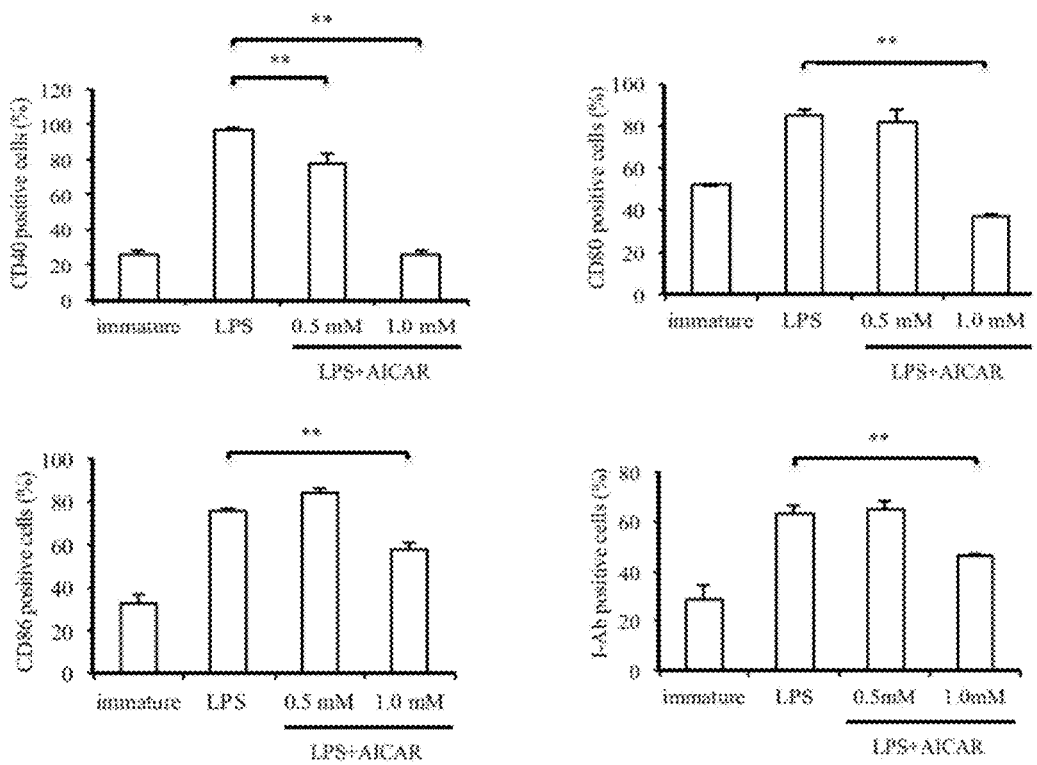
FIGS. 14A-14B depict the effect of AMPKα1 knock down and AICAR on BMDC maturation. BMDCs derived from AMPKα1KO mice were stimulated with LPS with or without AICAR.
Figure 14B:
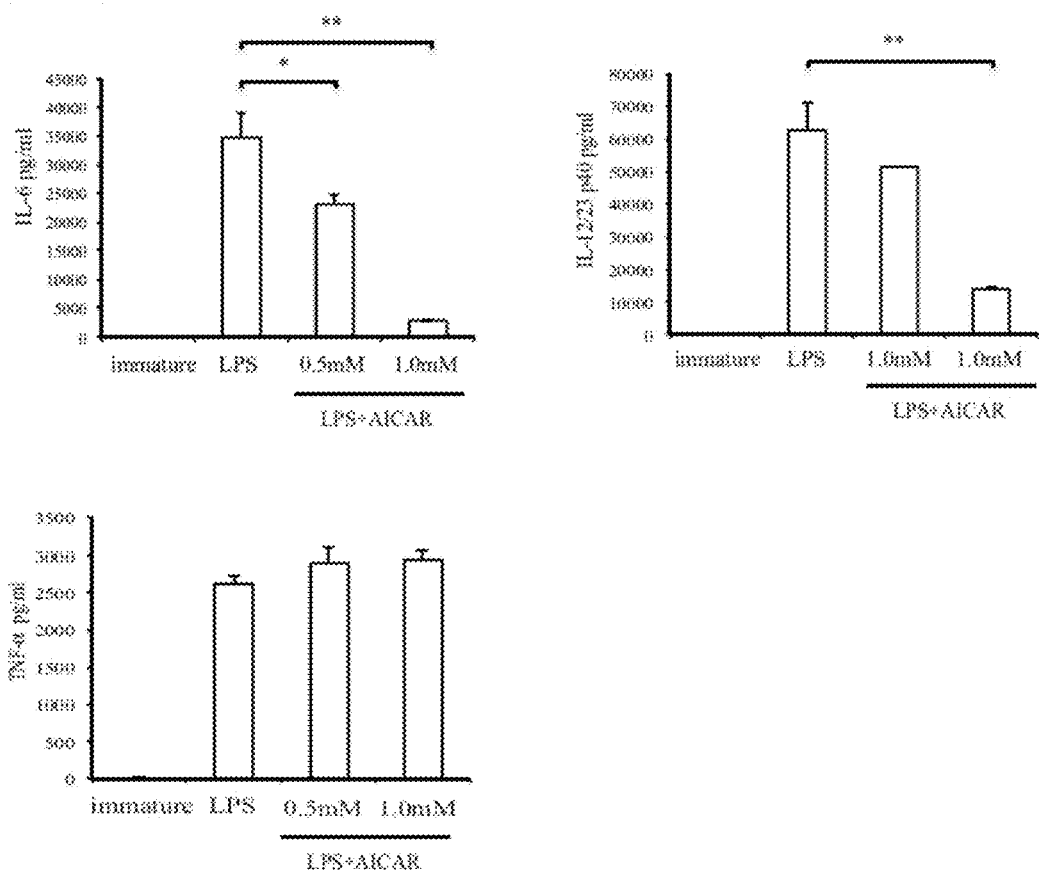

Since BMDCs expressed only AMPKα1, BMDCs were extracted from AMPK KO mouse and used to determine the role of AMPK in the anti-inflammatory effects of AICAR. As shown in FIGS. 14A and 14B, AICAR suppressed the maturation of AMPKα1 KO BMDCs. Specifically, AICAR significantly suppressed the expression of CD40, CD80, CD86 and I-A$^b$ in AMPKα1 KO BMDCs after LPS stimulation (FIG. 14A). Further, AICAR also suppressed the production of IL-6, TNF-α and IL12/23 $p^{40}$ in AMPKα1 KO BMDCs after LPS stimulation (FIG. 14B).

Figure 15:
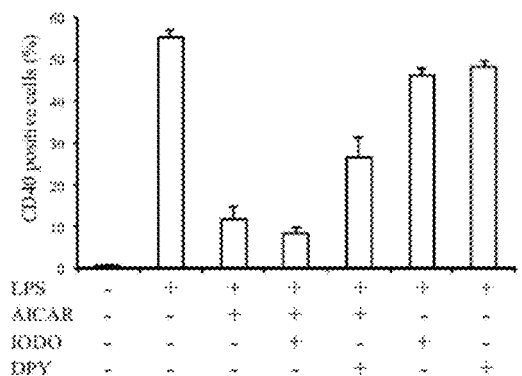
FIG. 15 depicts the combined effect of AICAR and a nucleoside transporter or an adenosine kinase inhibitor on BMDC maturation. WT BMDCs were stimulated with LPS and 1 mM AICAR in the presence or absence of 0.1 mM IODO or 1 μM DPY. The number of CD11c-gated CD40, CD80, CD86 and I-A$^b$ positive cells was measured by FACS. Bars represent mean±SD from three independent experiments.
Figure 15:
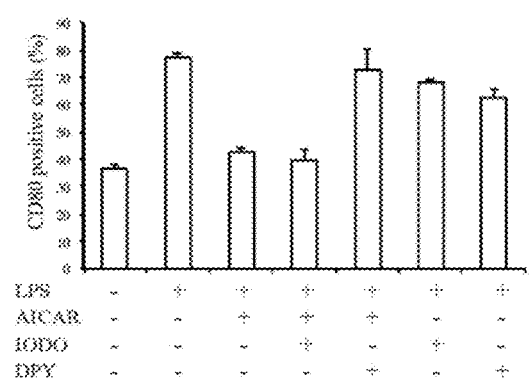
Figure 15:
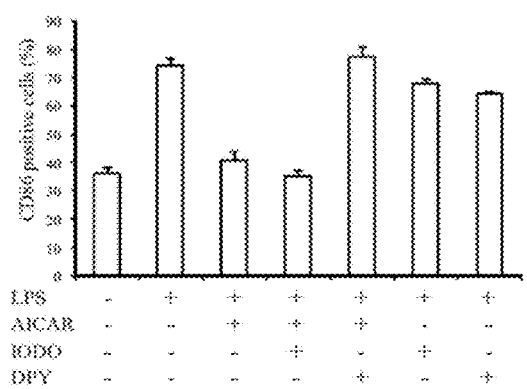
Figure 15:
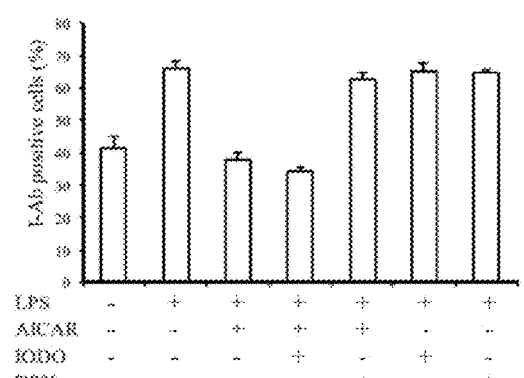

To further study AICAR's suppressive effect, an adenosine kinase inhibitor (IODO) was used to inhibit AICAR conversion to ZMP. In addition, an inhibitor of nucleoside transporter (DPY) was used to block AICAR translocation into cells. As demonstrated in FIG. 15, IODO did not affect the downregulation of co-stimulatory molecule expression by AICAR, suggesting that AICAR suppresses DC maturation mainly through an AMPK-independent pathway. However, DPY reversed the AICAR-mediated suppression of co-stimulatory molecule expression, indicating that the effects of AICAR are mediated via intracellular pathways.

INCORPORATION BY REFERENCE

The entire disclosure of each of the patent documents and scientific articles cited herein are incorporated by reference in their entirety for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method of treating macular edema in a subject in need thereof, the method comprising:
   administering AICAR or a pharmaceutically acceptable salt or ester thereof to the subject in an amount sufficient to ameliorate a symptom of the macular edema.

2. The method of claim 1, wherein the macular edema occurs as a result of age-related macular degeneration, cataract surgery, diabetes, drug toxicity, eye injury, retinal vein occlusion, or other inflammatory eye diseases.

3. The method of claim 1, wherein the macular edema occurs as a result of cataract surgery or diabetes.

4. A method of treating autoimmune uveitis or uveitis associated with type II, type III, type IV, or type V hypersensitivity reactions in a subject in need thereof, the method comprising:
   administering AICAR or a pharmaceutically acceptable salt or ester thereof to the subject in an amount sufficient to ameliorate a symptom of the uveitis.

5. A method of treating endophthalmitis in a subject in need thereof, the method comprising:
   administering 5-aminoimidazole-4-carboxamide-1-beta-d-ribofuranoside (AICAR) or a pharmaceutically acceptable salt or ester thereof to the subject in an amount sufficient to ameliorate a symptom of the endophthalmitis.

6. The method of claim 5, wherein the endophthalmitis is the exogenous form.

7. The method of claim 5, wherein the endophthalmitis is the endogenous form.

8. The method of claim 4, wherein from about 0.01 mg/kg to about 500 mg/kg of AICAR or a pharmaceutically acceptable salt or ester thereof is administered.

9. The method of claim 4, wherein from about 0.01 mg/kg to about 200 mg/kg of AICAR or a pharmaceutically acceptable salt or ester thereof is administered.

10. The method of claim 4, wherein about 0.5 mg/kg to about 100 mg/kg of AICAR or a pharmaceutically acceptable salt or ester thereof is administered.

11. The method of claim 4, wherein about 1 mg/kg to about 10 mg/kg of AICAR or a pharmaceutically acceptable salt or ester thereof is administered.

12. The method of claim 4, wherein the AICAR or the pharmaceutically acceptable salt or ester thereof is administered to the eye.

13. The method of claim 4, wherein the AICAR or the pharmaceutically acceptable salt or ester thereof is administered by intraocular injection.

14. The method of claim 4, wherein the AICAR or the pharmaceutically acceptable salt or ester thereof is administered intravitreally.

15. The method of claim 4, wherein the AICAR or the pharmaceutically acceptable salt or ester thereof is administered systemically.

* * * * *